(12) United States Patent
Klopotek

(10) Patent No.: US 12,350,144 B2
(45) Date of Patent: Jul. 8, 2025

(54) STABILIZATION OF COLLAGEN SCAFFOLDS

(71) Applicant: GEBAUER-KLOPOTEK PATENT VERWALTUNGS-UG, Neuhausen (DE)

(72) Inventor: Peter J. Klopotek, Neuhausen (DE)

(73) Assignee: Gebauer-Klopotek Patent Verw Altungs-UG, Neuhausen (DE)

( * ) Notice: Subject to any disclaimer, the term of this patent is extended or adjusted under 35 U.S.C. 154(b) by 419 days.

(21) Appl. No.: 16/728,941

(22) Filed: Dec. 27, 2019

(65) Prior Publication Data

US 2020/0146812 A1    May 14, 2020

Related U.S. Application Data

(63) Continuation-in-part of application No. 16/460,576, filed on Jul. 2, 2019.

(60) Provisional application No. 62/693,192, filed on Jul. 2, 2018.

(51) Int. Cl.
*A61F 2/14* (2006.01)
*A61F 9/008* (2006.01)

(52) U.S. Cl.
CPC .......... *A61F 2/142* (2013.01); *A61F 9/00827* (2013.01); *A61F 9/00836* (2013.01); *A61F 2009/00872* (2013.01)

(58) Field of Classification Search
None
See application file for complete search history.

(56) References Cited

U.S. PATENT DOCUMENTS

| | | | |
|---|---|---|---|
| 4,662,370 A | 5/1987 | Hoffmann et al. | |
| 4,676,790 A | 6/1987 | Kern | |
| 4,793,344 A | 12/1988 | Cumming et al. | |
| 5,288,436 A * | 2/1994 | Liu | A61F 2/142 264/447 |
| 5,342,378 A | 8/1994 | Giraud et al. | |
| 6,030,398 A | 2/2000 | Klopotek | |
| 6,099,541 A | 8/2000 | Klopotek | |
| 6,110,166 A | 8/2000 | Juhasz | |
| 6,296,650 B1 | 10/2001 | Carriazo | |
| 6,626,924 B1 | 9/2003 | Klopotek | |
| 2001/0053917 A1 | 12/2001 | Lin et al. | |
| 2007/0142908 A1 | 6/2007 | Xu | |
| 2007/0265650 A1 | 11/2007 | Pallikaris et al. | |
| 2010/0036488 A1 | 2/2010 | Juan, Jr. et al. | |
| 2010/0215717 A1 | 8/2010 | Soker et al. | |
| 2011/0183404 A1 | 7/2011 | Wee et al. | |
| 2012/0010728 A1 | 1/2012 | Sun et al. | |
| 2012/0310223 A1 | 12/2012 | Knox et al. | |
| 2015/0126453 A1 | 5/2015 | Xu et al. | |
| 2017/0119928 A1 | 5/2017 | Rzany et al. | |
| 2018/0228599 A1 * | 8/2018 | Elisseeff | C12N 5/0621 |
| 2019/0240003 A1 | 8/2019 | Klopotek | |
| 2019/0307551 A1 | 10/2019 | Peyman | |
| 2020/0000965 A1 | 1/2020 | Klopotek | |
| 2020/0146812 A1 | 5/2020 | Klopotek | |
| 2021/0113737 A1 | 4/2021 | Klopotek | |

FOREIGN PATENT DOCUMENTS

| | | |
|---|---|---|
| CN | 107233143 A | 10/2017 |
| EP | 1752119 A1 | 2/2007 |
| EP | 2138181 A1 | 12/2009 |
| EP | 2752192 A1 | 7/2014 |
| EP | 3509541 A1 | 7/2019 |
| KR | 20160140493 A | 12/2016 |
| WO | 2002006883 A2 | 1/2002 |
| WO | 2007121073 A2 | 10/2007 |
| WO | 2008136004 A2 | 11/2008 |
| WO | 2013081943 A1 | 6/2013 |

(Continued)

OTHER PUBLICATIONS

WO 2018219045 translation (powered by EPO and Google): 17 pages (obtained from the internet Mar. 3, 2023). (Year: 2018).*
Chae, J.J. Investigation of Biomaterials-Based Strategies for Corneal Reconstruction Thesis 2016: 178 pages. (Year: 2016).*
International Invitation to Pay Additional fees and Partial Search Report, PCT/IB2019/000779, dated Jan. 27, 2020, 12 pages.
International Search Report and Written Opinion, PCT/EP2020/087710, dated Apr. 13, 2021, 9 pages.
International Search Report and Written Opinion, PCT/IB2019/000779, dated Mar. 20, 2020, 18 pages.
International Search Report dated Dec. 15, 2017 from corresponding PCT/IB2017/055505, pp. 8.
International Written Opinion dated Dec. 15, 2017 from corresponding PCT/IB2017/055505, pp. 9.

(Continued)

*Primary Examiner* — Marsha Tsay
(74) *Attorney, Agent, or Firm* — Potomac Law Group, PLLC; Reza Mollaaghababa

(57) ABSTRACT

Shape-stabilized collagen scaffolds and methods of obtaining such scaffolds are disclosed. Stroma can be harvested, for example, from human or porcine corneal stroma and shaped during excision or in a separate step after excision. Following shaping (and preferably decellularization), the excised stroma portion is subject to pressure, force or vacuum to reduce fluid content and then irradiated or otherwise treated to induce crosslinking of collagen chains or fibrils. In one embodiment, the scaffold can be compacted by removing some or all of the water from the scaffold, and rehydrating the scaffold in a controlled manner (e.g., in a mold or other confining space) such that the scaffold takes a desired compacted shape; and then crosslinking at least a portion of the scaffold to mechanically strengthen it and inhibit subsequent swelling. Various sources of energy can be employed to induce crosslinking of collagen including, for example, ultraviolet (UV) radiation. The scaffolds can also be selectively densified or patterned. The invention is particularly useful in forming stable lenticules of enhanced stiffness and sufficient optical clarity for intracorneal implantation in additive ocular surgery.

37 Claims, 17 Drawing Sheets

(56) References Cited

FOREIGN PATENT DOCUMENTS

| WO | 2015010119 A2 | 1/2015 |
|---|---|---|
| WO | 2015188664 A1 | 12/2015 |
| WO | 2016178586 A2 | 11/2016 |
| WO | 2018029509 A1 | 2/2018 |
| WO | 2018047151 A1 | 3/2018 |
| WO | 2018219045 A1 | 12/2018 |
| WO | 2020008258 A2 | 1/2020 |
| WO | 2021130276 A1 | 7/2021 |

OTHER PUBLICATIONS

International Preliminary Report on Patentability, PCT/IB2019/000779, dated Jan. 14, 2021, 11 Pages.
Morishige, N., et al., "Three-dimensional analysis of collagen lamellae in the anterior stroma of the human cornea visualized by second harmonic generation imaging microscopy," Investigative Ophthalmology & Visual Science, vol. 52(2): 911-915 (2011).
Patel, S., et al., "Refractive index of the human corneal epithelium and stroma," Journal of Refractive Surgery, vol. 11 (2): 100-105(1995).
Chae, "Investigation of Biomaterials-Based Strategies for Corneal Reconstruction", 2016.
Cheng et al., "A structural model for the in vivo human cornea including collagen-swelling interaction", J.R. Soc. Interface, 2015.
Dahl et. al., "Corneal collagen cross-linking: An introduction and literature review" Optometry, 2012, vol. 83, pp. 33-42.
International Search Report for PCT International Application No. PCT/IB2016/054793 dated Feb. 15, 2017.
Machine translation of CN 107233143, 2024, 8 pages.
Moshirfar et. al., "Small-incision lenticule extraction", J Cataract Refract Surg, vol. 41, Mar. 2015.
O'Brart., "Corneal collagen cross-linking: A review", Journal of Optometry, 2014 7, 113-124.
Wilson, S.L., et al. 2016 Current Eye Research 41 (6): 769-782. (Year: 2016).
Written Opinion in PCT International Application No. PCT/IB2016/054793 dated Feb. 15, 2017.

* cited by examiner

STABILIZATION OF COLLAGEN SCAFFOLDS

RELATED APPLICATIONS

The present application is a continuation-in-part of U.S. Utility patent application Ser. No. 16/460,576 filed Jul. 2, 2019, which claims priority to U.S. Provisional Patent Application No. 62/693,192, filed Jul. 2, 2018, each of which is herein incorporated by reference in its entirety.

BACKGROUND OF THE INVENTION

Vision disorders caused by abnormal refractive conditions, e.g. ametropia, can be a significant problem for patients of all ages and can often, but not always, be treated with subtractive laser procedures. Recently, additive techniques have been developed which involve the transplantation of a lenticule into a patient's cornea after a flap has been cut and folded back to expose an intrastromal region of the cornea. The shape of the lenticule modifies the optical power of the patient's cornea by changing its curvature. The flap can then be replaced on top of the lenticule. In other situations, such as keratoconus, an implanted lenticule can mechanically stabilize or regularize abnormal stroma and slow disease progression. In keratoconus cases, a stromal pocket is more often formed rather than a flap.

However, several problems limit wider acceptance of additive (lenticular) techniques. First, the availability of donor human corneas to form lenticules is quite limited. Additionally, when lenticules are obtained from non-human sources, the lenticules must be decellularized to minimize immune reactions. Moreover, due to the nature of the lenticules (structured layers of collagen), they are fragile and require special handling. Generally, decellularization further weakens the structure and/or alters osmotic properties so that decellularized lenticules are prone to post-operative swelling, such that a proper refractive correction at the time of surgery may not remain so. Accordingly, there exists a need for better ways to stabilize implantable lenticules and other collagen-based scaffolds.

Collagen is widely present in the human body. For example, collagen is present in intestines, veins, joints, skin, internal membranes, ventricular valves as well as corneas.

However, the stromal collagen in the cornea is unique in many ways. Apart from water, collagen constitutes the major component of corneal stroma. Other components of stroma include glyco-amino-glycans (GAGs) and proteoglycans. Living cells constitute only about 1 to 4 percent of the corneal stroma. Human stroma consists of some 100-150 lamellae, each containing parallel collagen fibrils. In order to be transparent, the layers of collagen fibrils exhibit in-plane alignment with nearly ideal distribution of spacing between the layers or lamellae. No other organ contains collagen fibrils arranged in this manner.

Stromal collagen exhibits high tensile strength in the in-plane direction but is significantly weaker in the perpendicular-to-plane direction. Decellularized stroma exhibits further weakness. If such decellularized stromal collagen is to be used as a scaffold, better methods of augmenting its mechanical strength are needed.

SUMMARY OF THE INVENTION

Methods of stabilizing collagen scaffolds are disclosed whereby water extraction and/or compression, (or desiccation and controlled rehydration), as well as crosslinking, can be employed to shape the scaffold, mechanically strengthen it, and inhibit its tendency swell in aqueous environments. The methods can be particularly useful in preparing collagen scaffolds as lenticules for intrastromal or intracorneal implantation as part of additive refractive surgery.

Scaffolds formed from collagenous tissue can provide mechanical advantages to the cornea. However, because scaffolds are typically mechanically weakened by decellularizing processes, they need to be strengthened and oriented before being placed into or upon the stroma. In one aspect of the invention, methods of forming and strengthening a scaffold from donor collagenous tissue are disclosed that include the steps of excising a portion of tissue from a central region of a donor collagenous tissue source (e.g., donor corneal stroma); shaping the tissue portion to provide a scaffold of a first desired shape; decellularizing the scaffold; compacting the scaffold (e.g., in direction generally perpendicular to the scaffold's lamellar structure) to remove excess fluid present in the scaffold and enhance collagen density; and crosslinking at least a portion of the scaffold to mechanically strengthen and inhibit subsequent swelling when the scaffold is exposed to an aqueous environment.

Alternatively, the methods of the present invention can be practiced by excising a portion of tissue from a central region of a donor collagenous tissue source (e.g., donor corneal stroma); optionally shaping the tissue portion to provide a scaffold of a first desired shape; decellularizing the scaffold; compacting the scaffold by removing some or all of the water from the scaffold, and rehydrating the scaffold in a controlled manner (e.g., in a mold or other confining space) such that the scaffold takes a desired compacted shape; and then, again, crosslinking at least a portion of the scaffold to mechanically strengthen and inhibit subsequent swelling when the scaffold is exposed to an aqueous environment.

Accordingly, the methods of the present invention can enhance a collagen scaffold's mechanical strength and chemical stability. Crosslinking can also be employed to restore and/or preserve the optical clarity (e.g., transparency) of the scaffold when it is intended for use as an intracorneal implantable lenticule.

In certain embodiments, the steps of excising and initial shaping can be performed simultaneously. The step of decellularizing the scaffold can further include lysing cells and removing cellular debris from the lenticule with a detergent or a surfactant; and optionally can further include enzymatically removing at least one immunogenic epitope from the lenticule. One solution useful in decellularizing the scaffold can comprise water, ethyl alcohol and glycerol. The decellularizing solution can also be used to compact the scaffold if a controlled rehydration step is employed. Alternatively, decellularization can be followed by desiccation. Orientation of the scaffold can also be manipulated. Method steps recited herein, whenever feasible, can be performed in any order.

Without being bound by any particular theory of operation, mechanical strengthening of the collagen scaffolds is not only the result of crosslinking but also the result of compaction (or confinement) of collagen fibrils into tighter bundles. Crosslinking of densified fibril bundles can result in material strength beyond the improvement achievable by crosslinking alone.

In the methods of the present invention, the step of crosslinking can further include exposing at least a portion of a compressed scaffold to a crosslinking agent or energy mediating agent or exposing at least a portion of the compressed (or confined) scaffold to radiation to induce crosslinking by peptide bond formation between collagen fibrils with or without the assistance of an energy mediating agent. The combination of chemical and photo-crosslinking is also disclosed, whereby the chemical agents may induce different chemical bonds and physically form mechanical bridges between the collagen fibrils.

The step of crosslinking can be conducted by exposing at least a portion of a compressed (or otherwise compacted) scaffold to radiation by direct exposure, or by exposure to such radiation at a grazing angle or via an evanescent waveguide coupled to a surface of the scaffold. The crosslinking can further include exposing a surface portion of the compressed scaffold to a radiation such that a surface portion exhibits greater crosslinking and higher collagen density than a bulk region of the scaffold.

Preferably, the steps of compressing/compacting and crosslinking result in at least a portion of the scaffold having a collagen density greater than the initial decellularized scaffold segment. For example, at least a portion of the compressed and crosslinked scaffold can have a composition of at least 20 percent collagen, preferably more than 35 percent collagen.

The methods of the present invention can be practiced such that the scaffold is configured for use as an implantable intracorneal lenticule having a lenticule body, an oriented anterior surface and a posterior surface and the method further comprises treating at least a portion of the posterior surface of the lenticule with a crosslinking agent or by selective application of patterning radiation to promote adherence of the lenticule to a stromal bed. In certain embodiments, the methods can include the steps of: forming a lenticule from donor stroma, removing a portion of tissue from a central region of a donor stroma by lenticule extraction, shaping the removed tissue portion into a lenticule of a first desired shape, the lenticule having a lenticule body, an anterior surface and a posterior surface, removing cellular material from the lenticule; removing excess fluid present in the lenticule (e.g., water originally present in the stroma and any other fluids that may have been introduced into the lenticule during decellularization); and crosslinking at least a portion of the lenticule to define a final desired shape and inhibit subsequent swelling when the lenticule is exposed to an aqueous in vivo environment. Lenticule formation can be carried out by lenticule excision or extraction performed with a keratome or a femto second laser or excimer laser or a water jet.

Crosslinking of the lenticule can be conducted by exposing at least a portion of the compressed scaffold to a crosslinking agent or energy mediating agent or by exposing at least a portion of the compressed scaffold to radiation to induce crosslinking by peptide bond formation between collagen fibrils with or without the assistance of an energy mediating agent. For example, crosslinking of a lenticule can include exposing at least a portion of the compressed scaffold to radiation by direct exposure, or by exposure at a grazing angle or via an evanescent waveguide coupled to a surface of the scaffold. In certain applications ultraviolet radiation is the preferred energy source.

Chemical methods of crosslinking of collagen can also be employed. These methods can include the use of chemical agents (e.g., genipin) or photochemical agents. For example, U.S. Patent Application Pub. No. 2017/0119928 discloses methods of forming heart valve prostheses by decellularizing pericardial tissue to obtain a collagenous matrix material that can be crosslinked with a glutaraldehyde-containing solution and shaped into a desired structure for implantation.

Radiation crosslinking can be advantageous over chemical crosslinking because the resulting lenticule is frequently more transparent—resulting in better visual acuity following implantation in a recipient cornea.

Radiation crosslinking of the compacted scaffolds can be achieved with substantially less energy than that necessary for non-compacted (fluid laden) scaffolds. For example, for a typical lenticule following compaction, crosslinking can be achieved by ultraviolet radiation with a fluence of less than about 15 Joules/cm$^2$ or in some instances less than about 2500 Joules/cm$^2$. More generally, the desired fluence will range from about 15 Joules/cm$^2$ to about 600 Joules/cm$^2$. One particular range of wavelengths useful for crosslinking collagenous scaffolds generally corresponds to part of the "UV-C" wavelength band, e.g., from about 185 nm to about 280 nm. Other UV wavelength bands (the UV-B band ranging from about 280 nm to about 315 nm (or 320 nm) or the UV-A band from about 315 nm (or 320 nm) to about 400 nm) can also be employed as well as X-rays, gamma radiation or electron beams in some instances to induce at least partial crosslinking and/or sterilization of the scaffolds.

Because a decellularized collagen scaffold exhibits some amount of "shape memory" or "compressional hysteresis" it is possible to separately compress it and thereafter to cross-link it while it is no longer constrained by the compression mold. This separation (sequentially) is an alternative manufacturing process. However, the preferred method in most instances is to induce crosslinking while the scaffold remains compressed/compacted in the mold. In either case the crosslinking of compacted collagen bundles results in greater strength than crosslinking of a dispersed collagen fibrils arrangement.

In another aspect of the inventive methods, the step of crosslinking can further include the step of exposing a surface portion of the compressed scaffold to a radiation such that a surface portion exhibits greater crosslinking and higher collagen density than a bulk region of the scaffold. Moreover, the step of crosslinking can also include applying sufficient radiation to inactivate any microbial agents and sterilize the lenticule. In certain embodiments, the step of decellularizing the scaffold can encompass removing cellular debris from the lenticule with a detergent or a surfactant; and optionally further comprises enzymatically removing at least one immunogenic epitope from the lenticule.

Additionally, the steps of compressing and crosslinking can result in at least a portion of the scaffold having a collagen density greater than the initial collagenous tissue segment. The step of crosslinking can further include selectively applying radiation to the anterior surface such that an anterior surface region exhibits a greater degree of crosslinking or greater collagen density than a bulk region of the lenticule body.

In another aspect of the invention, crosslinking can also advantageously modify the "stiffness" of the lenticules and scaffolds formed by the present teachings. In mammalian corneal tissue most collagen fibrils are aligned "horizontally" (or alternatively expressed, tangentially to the corneal surface). The fibrils are made of very long collagen molecules wound in primary, secondary and/or tertiary coils.

According to the present teachings, several distinct types of crosslinking can be induced. For example, crosslinking can be induced within the tertiary coils of collagen as a kind of collagen-collagen bridge. This crosslinking can decrease the longitudinal elasticity collagen fibrils (e.g., stiffen) by making individual coils adhere more strongly stronger to each other. The rate of this crosslinking is less sensitive to the scaffold compression, as the coils are oriented "horizontally" and the compression largely does not influence the compactness of individual fibrils. The amount of this kind of crosslinking is generally proportional to the cumulative radiation dosage and the state of compression/compaction is of limited significance. This first type of crosslinking makes the corneal tissue more resilient to stretching in direction "parallel/tangential" to the surface, as it is the case of stroma stretching by the intraocular fluid's IOP.

A second kind of crosslinking can occur between collagen belonging to different (albeit neighboring) collagen strands or fibrils. This bridges typically do not involve a direct collagen-collagen bond, but rather the connection is mediated (bridged) by other molecules such as GAGs or proteoglycans. In contrast to the first type, this second type of crosslinking is very sensitive to the compression/compaction of the scaffold and can induce three distinctive changes to mechanical property/behavior to the scaffold.

Secondary crosslinking (mediated by bridge molecules between fibrils) increases swelling resistance. This resistance is a direct expression of the "vertical" (radial) stiffening of the lenticule or scaffold. The vertical bridges resist changes in the distance between neighboring fibrils. Secondary crosslinking also induces resistance to osmotic collapse of the scaffold when implanted into human stroma. This resistance results from compaction and consequent higher concentration (per unit volume) of GAGs and proteoglycans, which will exert a higher (or at least equal) osmotic pressure than the native stroma of the recipient. Moreover, secondary crosslinking will restrain slip-sliding between layers of collagen fibrils. This restraint stiffens the scaffold against bending forces relative to the native human stroma.

Decellularization of donor tissue, by itself, partially removes (degrades) the tissue's GAGs and proteoglycans, such that the decellularized tissue exhibits lower osmotic pressure than of the native human stroma (about 50-60 mm Hg) and can cause collapse of the scaffold upon the implantation. Compression (or compaction), on the other hand, can restore the full osmotic pressure of the scaffold, albeit at lower thickness than the original thickness of the donor's lenticule (before decellularization). Collagen as hydrophobic material contributes very little to the osmotic properties. However, the increased concentration of the GAGs and proteoglycans (in smaller space) enhances their contribution the osmotic pressure. In other words, compression/compaction compensates for the decellularization loss of GAGs and proteoglycans and restores their concentration but in smaller volume.

Thus, crosslinking permits one to lock in the enhanced osmotic properties of the compacted lenticule to prevent swelling during formation while also preventing collapse of lenticule in vivo after the implantation when osmotic interactions come into play. In other words: crosslinking according to the present teachings stabilizes the lenticule osmotically in both ways, pre and post implantation.

In another aspect of the invention, lenticules and scaffolds of increased stiffness can be obtained by the present teachings. The stiffness of the crosslinked collagen can be quantified, for example, by the parameter, $\mu$, called modulus. The nominal standard value for the modulus, $\mu$, of native human corneal collagen can vary across the population. For example, for young human eyes, the average modulus, $\mu$, of corneal collagen can be about $5 \times 10^4$ Pascal (Pa). For older individuals, the modulus, $\mu$, can be as high as $1.2 \times 10^5$ Pa. Moreover, for porcine eyes (which can be an important source of implantable lenticular and scaffold collagen) the average modulus, $\mu$, of corneal collagen can be as low as about $2 \times 10^4$ Pascal (Pa).

As a result of compaction and crosslinking according to the present teachings, collagenous lenticules and scaffolds can be obtained exhibit a modulus stiffness, $\mu$, greater than $2 \times 10^4$ Pa, or greater than $8 \times 10^4$ Pa, or greater than $1.6 \times 10^5$ Pa, or greater than $2 \times 10^5$ Pa, or greater than $3 \times 10^5$ Pa, or greater than $5 \times 10^5$ Pa, or greater than $8 \times 10^5$ Pa, or greater than $1 \times 10^6$ Pa, or greater than $3 \times 10^6$ Pa, or greater than $5 \times 10^6$ Pa, or greater than $1 \times 10^7$ Pa.

For example, lenticules (including scaffolds) according to the present teachings can exhibit a modulus value, $\mu$, ranging from $1 \times 10^4$ Pa to $1 \times 10^7$ Pa, or from $2 \times 10^4$ Pa to $8 \times 10^6$ Pa, or from $1 \times 10^5$ Pa to $5 \times 10^6$ Pa, or from $3 \times 10^5$ Pa to $5 \times 10^6$ Pa, or from $1 \times 10^6$ Pa to $2.6 \times 10^6$ Pa.

In yet another aspect of the invention, decellularized collagen lenticules are disclosed having a lenticular body derived from donor tissue having an anterior surface and a posterior surface that are formed to provide the lenticule with a desired shape and orientation. For example, the lenticules can have convex and concave sides that coincide frequently, but not always, with the anterior and the posterior surfaces of the lenticules. The lenticular body can include layers of collagen that have been decellularized and compressed/compacted to achieve a composition that is greater than 15 or 25 percent collagen and can further be at least partially crosslinked to inhibit axial swelling. For bulk crosslinked lenticules, the composition can be greater than 30 percent collagen. Moreover, if locally densified layers are desirable (e.g., to approximate corneal structures such as Bowman's Membrane) the local collagen concentration can be even higher (e.g., greater than 35 percent or greater than 40 percent or even greater than 60 percent collagen).

The lenticule can be characterized in certain embodiments by layers of collagen that are crosslinked by application of radiation and the lenticule can also be further characterized by induced peptide bonds between collagen fibrils. The lenticule can be from 90 percent to 100 percent, or preferably from 95 percent to 99.99 percent, free of cellular material and formed in a desired shape such that following decellularization, compression and crosslinking, the lenticule can be implanted into a patient's eye to change the refractive power of the cornea or replace or reinforce damaged or diseased areas of the stroma.

Lenticules according to the invention typically have a curved, disc-like shape and a diameter of about 0.5 mm to about 10 mm. They also typically have a maximum thickness that can range from about 600 to about 50 micrometers, more preferably from about 400 to about 100 micrometers. The lenticules are typically not of uniform thickness and the minimum thickness can be less than about 50 micrometers, more preferably less than about 30 micrometers or less than about 15 micrometers.

The lenticules should exhibit low immunoreactivity due to degradation of immunogenic epitopes. In certain embodiments at least one surface of the lenticule further includes a pattern of variable crosslinking to promote adherence of the lenticule to a stromal bed when implanted intrastromally into a patient's stromal bed. The lenticules can also have an anterior surface with an anterior surface region having a greater collagen density than a bulk region of the lenticule body. For example, the collagen density of the anterior surface region can be at least about 35 percent or 40 percent or 60 percent collagen.

Thus, the present invention discloses methods of stabilizing the shape of collagen lenticules and scaffolds. Collagenous tissue can be harvested from any collagenous source of human or animal origin. In certain preferred embodiments, the tissue can be harvested from human or porcine stroma. The source tissue can be shaped during excision or in a separate step after excision. The tissue can be shaped, decellularized and stabilized by various techniques, several of which are described in more detail below. Following shaping and decellularization, the excised collagenous tissue segment is subject to compression/compaction to reduce fluid content and irradiated to induce crosslinking of collagen chains or fibrils. Crosslinking can be induced with or without chemical intermediaries, e.g., crosslinking agents. In certain preferred embodiments, crosslinking is achieved by formation of peptide bonds between collagen fibrils by exposure to sufficiently energetic radiation. This energetic radiation is desirable as the creation of peptide bonds between the collagen chains is typically an endothermic reaction. Various sources of energy to induce peptide bond crosslinking can be employed. In certain preferred embodiments, the energy is delivered by ultraviolet (UV) radiation.

The invention is particularly applicable for spatial stabilization of collagen scaffolds harvested from layered collagenous tissues, in general, and the corneal stroma, in particular. The layered collagen arrangement of the source tissue may have naturally evolved for optical transparency but can result in mechanical weakness and/or osmotic tendency to swell when exposed to aqueous environments. Thus, an object of the present invention is to inhibit such swelling and/or provide greater axial mechanical strength to the final scaffold. The invention can also be applied to unlayered (or chaotic) excised collagenous tissue segments.

In another aspect of the invention, methods are disclosed for altering the collagen density or smoothness on at least one surface of the scaffold, e.g., on the anterior surface, if the scaffold is a lenticule intended for corneal implantation. Such a surface alteration can make the scaffold easier to manipulate post implantation, e.g., if an overlying flap must be reopened to access the implant. The surface alteration can be achieved by irradiation and/or the application of chemical agents.

Decellularized and shaped corneal tissue lenticules from allograft and/or xenograft sources and methods of obtaining such lenticules are disclosed. The lenticules are particularly useful as intrastromal or intracorneal lenticular implants in keratoplasty procedures, in which a hinged flap is formed in a patient's cornea and folded back along its hinge to expose the stromal bed of the cornea. The shaped lenticule is then applied to the stromal bed and the flap returned to its original position imparting a new curvature to the cornea and resulting in a desired refractive correction. Fine-tuning of the new refractive power can be achieved by laser ablation either at the same time as implantation or at later time in the event of regression or tonus changes.

In one aspect of the invention, decellularized corneal lenticules and methods of decellularizing cornea tissue are disclosed to reduce potential immunogenic reactions on the part of the patient to the implanted lenticule. Only about 1-4 percent of the typical cornea is composed of cells. The other 96-99 percent is largely extracellular matrix (ECM)—primarily collagen, glyco-amino-glycans (GAGs) and proteoglycans, and water. In one preferred embodiment, the cellular component of the lenticule is removed by treatment with a surfactant, such as for example, sodium tetradecyl sulfate (STS), or by enzymatic solubilization. If desired, additional steps can be taken to further reduce the immunogenicity of the lenticule, especially if the source is a non-human (xenogeneic) donor. For example, two non-human epitopes that may be present in xenogeneic tissue are neu5GC and Alpha-Gal. These undesirable epitopes may be present not only inside or on the surface of stromal cells; a fraction of the epitopes may be embedded inside the GAGs, also known as mucopolysaccharides, that wrap around ECM collagen fibrils. In such cases, such epitopes can be selectively removed, at least partially, by kinase treatments and additional washing.

The decellularized lenticules of the present invention typically have 95%-100% of cellular materials removed. Preferably, the lenticules are 95%-99.99% cell-free. Without reciting every possible sub-range between 95% and 100%, it should be clear that all such sub-ranges are contemplated and considered part of the invention. For example, the lenticules can be 95% to 97%, 97% to 99% or 98% to 99.9% free of cellular materials.

In another aspect of the invention, disc-shaped lenticules according to the invention are obtained by cutting a disc-shaped tissue segment from a donor cornea. The tissue segment can be sliced and/or further shaped or cut in such a manner that the desired shape is obtained during the slicing procedure. Cutting can be performed mechanically, e.g., with a microkeratome or the like, by laser processing, e.g., or by photo-cleavage with a femtosecond laser or by an excimer laser or by a water jet. To reduce the possibility of asymmetry, the tissue segment is preferably taken from the central portion of the donor cornea, e.g., with the optical or geometrical axis of the donor cornea preserved at the center of the lenticule. The shape of the tissue segment will be dictated by the dioptric power change needed to correct the patient's refractive error. For example, for correction of hyperopia (hypermetropia) and/or presbyopia, the goal is typically to increase the curvature of the cornea and the desired lenticule shape will be slightly convex on at least one side. Typically, the maximum thickness of the lenticule will be less than 400 micrometers, or in many instances less than 200 micrometers, or less than 100 micrometers, or less than 50 micrometers. Maximum thickness for almost all applications is less than 600 micrometers. In some circumstances a visual improvement in patients suffering from macular degeneration can be achieved if the said disc-lenticule is formed as a prism redirecting light to a different portion of the retina.

The treatment of keratoconus can include not only reduction of visual aberrations but only mechanical reinforcement of the diseased stroma. A co-planar disk of thickness between 50 and 300 micrometers, with transitional slanted (wedge like) zone on the disk's perimeter, may be preferable for this purpose. Alternatively, lenticules for treatment of keratoconus can take advantage of the natural curvature inherited from the donor cornea—or an additional degree of curvature can be introduced during compression/compaction and/or crosslinking by use of a curved mold. In some instances, it may be advantageous in treating keratoconus to implant a lenticule "upside-down" e.g., such that the lenticule's curvature is the opposite of the recipient cornea.

While curved molds may be desirable in some instances, the steps of compression/compaction and crosslinking can also be executed with flat molds. (Flat molding can be advantageous for storage and transportation or efficiency of manufacturing.) In another aspect of the invention hermetically-sealable molds can be employed for both compression/compaction and storage.

Pressure applied to one surface of the scaffold can also be used to change its curvature and/or to realign (or maintain the alignment of) collagen fibrils. For, example, a scaffold can be secured to an opening in a chamber, which is then filled with a pressurized fluid to assert pressure on one side of the scaffold, imparting horizontal/tangential forces to the scaffold. The fluid pressure will cause the scaffold to expand (like a balloon). A compressive plate can optionally be applied to an opposite surface. For example, a curved (quasi-concave) compression plate can be used to limit the extent to which the scaffold can be stretched or reshaped. When the desired curvature is obtained, crosslinking can be employed to maintain the desired shape and/or inhibit the tendency of so-manipulated scaffolds to swell upon intrastromal or intracorneal implantation.

In some embodiments, it may be advantageous to preserve the top stromal surface, i.e., the so-called "Bowman's membrane" such that the anterior surface of the lenticule will exhibit a different texture than the other (posterior) surface because this naturally anterior segment of the cornea is denser and smoother due to natural condensation of the outermost layers of stromal tissue. Alternatively, the excised segment can be taken from the central region of the stroma and an anterior surface can be densified following shaping and excision by selective crosslinking as described in more detail below. The posterior surface (opposite to anterior surface or Bowman's membrane) will be rougher due to lesser stromal tissue density and the fact that it is formed by mechanical or laser cutting of the tissue. This difference in roughness can be especially advantageous when the lenticule is used for intrastromal or intracorneal implantation because it can be highly desirable that the lenticule be strongly adherent to the stromal bed. If a less than optimal refractive result is observed post procedure, the flap may need to be folded back again to permit further keratoplasty (re-sculpting of the lenticule) by laser ablation or the like. Any movement of the lenticule from its original position in the stromal bed could compromise the effectiveness of this keratoplasty. Moreover, the smoothness of the anterior surface of the lenticule also makes it less likely that reopening the flap will dislodge the lenticule.

In yet another aspect of the invention, the posterior surface can be treated following excision, shaping and decellularization to make the surface more adherent to the stromal bed. For example, a crosslinking agent can be applied, prior to sterilization and packaging. Alternatively, the adherence-enhancing agent can be applied by the clinician during the procedure before implantation. The anterior surface can be treated to make it less adherent to the flap.

BRIEF DESCRIPTION OF THE DRAWINGS

FIG. 8A shows a lenticule with a simple, e.g., cylindrical or conical peripheral edge;

FIG. 8B shows a lenticule with a zig-zag or step-shaped edge at its periphery;

FIG. 10A shows the mold is shown before the compression of the scaffold;

FIG. 10B illustrates the mold after compression;

DETAILED DESCRIPTION

Figure 1A:
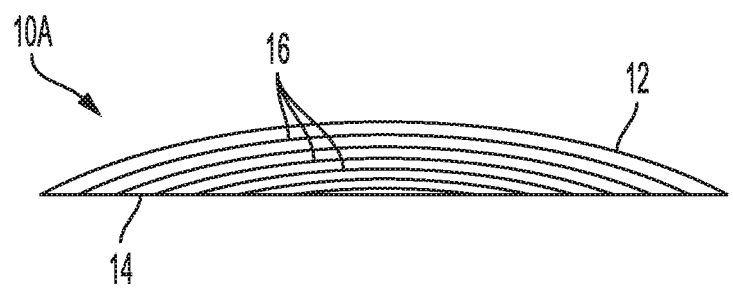
FIG. 1A is a schematic, cross-sectional illustration of an excised stromal tissue segment.

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

The term "cutting" encompasses any of known methods of dissection, ablation or removal of biological material, e.g., by action of mechanical blades, ultraviolet (UV) lasers, femto second lasers, or water jets.

The terms "compression," "compressed," and "compressing" encompass compaction by application of pressure or by other techniques such as vacuum or centrifugal force-driven water extraction. The term "compression" is also used generally to describe dehydration and controlled rehydration in a confined spaced such that the scaffold or lenticule has a desired density. The terms "confined" and "reconstituted" are also used to describe the process of dehydrating (or desiccating) a tissue portion and controlled rehydration (or swelling) in a constraining chamber to achieve a lenticule or scaffold of desired shape and density.

The term "radiation" encompass infrared radiation, visible radiation and ultraviolet radiation (e.g., from about 400 nm down to approximately 193 nm or below), X-rays, gamma rays, and electron beams.

The term "biological sample" refers to tissue, cells, cellular extract, homogenized tissue extract, or a mixture of one or more cellular products. The biological sample can be used or presented in a suitable physiologically acceptable carrier.

As used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 100 μm means in the range of 90 μm-110 μm. It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The terms "animal," "patient," or "subject" as used herein includes, but is not limited to, humans and non-human vertebrates such as wild, domestic and farm animals. The terms "animal," "patient," or "subject" also refers to the recipient of a corneal lenticule transplant. The term "xenograft" refers to tissue collected from animals for donation, including pigs (porcine), bovine, apes, monkeys, baboons, other primates, and any other non-human animals. "Allograft" refers to tissue taken from a donor that is the same species as the recipient.

Generally speaking, the term "tissue" refers to any aggregation of similarly specialized cells which are united in the performance of a particular function. The corneal stroma is an example of "tissue" even though it is largely acellular (about 1 to 5 percent cellular).

The terms "desiccating," "desiccated," and the like, refer to the removal of some or all of the water in a tissue portion. For example, "desiccation" can remove between 50% and 100% of the water present in the tissue, preferably in some instances between 60% and 95% of the water. Typically, to achieve a desired degree of compaction, "desiccation" can be practiced by removing at least 30%, or at least 40%, or at least 50%, or at least 60%, or at least 70%, or at least 80%, or at least 90%, or at least 95%, or at least 98%, or at least 99%, of the water in a tissue portion. Desiccation can be achieved through chemical processes, such ethanol fluid exchange, or via physical means, such as vacuum drying or lyophilization (e.g., in a dry ice containing chamber—or another freeze drying apparatus).

The term "lenticule" refers to a decellularized, processed donor corneal tissue ready for implantation into or onto a recipient's cornea. Unless otherwise indicated, the terms "lenticule" and "scaffold" are used interchangeably herein. When used, each term is intended to encompass the other. The terms "collagen concentration" and "collagen percentage" are used interchangeably herein and refer to amount of collagen present in the lenticule or scaffold. This concentration or percentage can be measured as the fractional weight of a completely desiccated lenticule, e.g., a vacuum desiccated lenticule, relative to the weight of the lenticule before desiccation (in full equilibrium with water). In some cases, ethanol can be used to improve desiccation.

The term "intracorneal" in the context of lenticule implantation refers to any procedure in which a lenticule is placed in or on the cornea. One type of intracorneal implantation is "intrastromal" implantation, a procedure in which a lenticule is placed within the stroma of the eye, without excision of the anterior Bowman's membrane or epithelium, e.g., by the folded back of a flap of anterior tissue or by direct insertion via a lateral approach. Other types of intracorneal use of lenticules include deep anterior lamellar keratoplasty (DALK) and penetrating keratoplasty (PK), in which a lenticule replaces an anterior segment of the eye completely, as discussed in more detail below. Yet another applicable "intracorneal" procedure is so-called "epikeratoplasty," also discussed in more detail below.

The term "axial" refers a direction relative to the orientation of the lenticule or scaffold. Typically, the shaped lenticule will be curved in spheroidal or ellipsoidal disc-like shape and the axial direction or "axis" will be generally perpendicular to the center of the disc. Unless otherwise indicated, "axial" is also generally almost parallel to, or coaxial with, the visual or optical axis of an eye from which the tissue segment is excised or the recipient eye where the lenticule is designed to be implanted. (In a natural eye, the optical axis typically goes almost, but not exactly, through the center of the cornea.)

Planetary physics (spherical geometry) can provide a convenient nomenclature to describe the spatial arrangement of collagen fibrils in stroma. Most of the collagen fibrils are on high to middle latitude orbits and only a minor portion resides in polar orbits. For this reason, the stroma is typically thinnest in the central (middle) region/location. The axial direction of the compression can be called polar cap compression or radial compression. The central region of donors stroma exhibits a strong rotational symmetry in fibril alignment. In cases where the implant is designated to work not only in compression but also under tensile stresses, lenticules extracted from a central stromal location is preferable to impart rotationally symmetric tensile properties to the implant.

This disclosure also relates to a decellularized corneal lenticule from allograft and/or xenograft sources and methods of forming a lenticule from donor stroma. The disclosed decellularized corneal lenticules can be used to correct abnormal refractive conditions, such as myopia, hyperopia, presbyopia, and astigmatism, as well as other ophthalmic pathologies.

The cornea can be generally considered to be comprised of 5 layers, from anterior to posterior: the corneal epithelium, a thin but dense top stromal layer (typically referred to as Bowman's membrane in human eyes), the corneal stroma, Descemet's membrane, and the corneal endothelium. The corneal epithelium is composed of about 6 layers of non-keratinized stratified squamous epithelium cells, which are fast growing and easily regenerated. The anterior stromal layer (e.g., Bowman's membrane) is a tough layer composed mostly of randomly organized, tightly woven collagen type I fibrils. The corneal stroma is a thick, transparent layer consisting of collagen type I fibers arranged in parallel layers. The Descemet's membrane is a thin acellular layer that serves as the basement membrane of the corneal endothelium and composed of less rigid collagen type IV fibrils. Finally, the corneal endothelium is composed of simple squamous or low cuboidal monolayer of mitochondria-rich cells.

As used here, the term "Bowman's membrane" is used to describe the anterior stromal region of any cornea from either human or a donor animal cornea. Although the densified stratum of the human cornea can be more pronounced (and, hence, known as Bowman's membrane in human corneas), all corneas exhibit some higher anterior densification and smoothness (relative to stromal bed tissue) to some degree depending on animal species and age. Hence, "Bowman's membrane" is a term used throughout the present application to describe this anterior segment.

As such, the harvesting and processing of donor corneas and the production of lenticules is a crucial element to correction of refractive errors in vision. The lenticules are particularly useful as lenticular implants in keratoplasty procedures, in which a hinged flap is formed in a patient's cornea and folded back along its hinge to expose the stromal bed of the cornea. The shaped lenticule is then applied to the stromal bed and the flap returned to its original position yielding a new curvature to the cornea and resulting in a desired refractive correction. Fine tuning of the new refractive power can be achieved by laser ablation either at the same time as implantation or at later time in the event of regression or tonus changes.

In certain embodiments of the invention, a decellularized corneal lenticule can include a lenticular body derived from donor stroma having an anterior surface that includes at least a portion of top layer from the donor stroma and a posterior surface that is formed to provide the lenticule with a desired shape; and wherein the donor stroma is decellularized. In other embodiments, the lenticule is shaped without regard to the preservation of Bowman's membrane and any top portion of donor stroma. For example, the lenticule can be formed by intrastromal excision of a stromal tissue segment, e.g., by excision with femtosecond laser pulses.

In certain embodiments, the donor stroma is harvested and decellularized, producing lenticules with a reduction in any potential immunogenic reaction on the part of the patient. Only about 1 to about 4 percent of the typical cornea is composed of cells. The other 96 to 99 percent is largely extracellular matrix (ECM), primarily collagen, and water, glyco-amino-glycans and proteoglycans. As noted above, the decellularized lenticules of the present invention typically have 95%-100% of cellular materials removed. Preferably, the lenticules are 95%-99.99% cell-free. Without reciting every possible sub-range between 95% and 100%, it should be clear that all such sub-ranges are contemplated and considered part of the invention. For example, the lenticules can be 95% to 97%, 97% to 99% or 98% to 99.9% free of cellular materials. The amount of cellular material remaining in the lenticule can be measured, for example, by residual DNA or RNA content. Preferably, the DNA or RNA content is less than one percent, or less than 0.1 percent, or less than 0.01 percent by weight of the original DNA or RNA content.

Decellularization, i.e. the removal of cellular material from the donor stroma, can be accomplished using a variety of techniques. In one preferred embodiment, the cellular material of the cornea is removed by chemical treatment. The chemicals used to lyze and remove cells from the cornea include surfactants, such as, sodium tetradecyl sulfate (STS), acids, alkaline treatments, ionic detergents, such as sodium dodecyl sulfate (SDS), non-ionic detergents, such as, Triton X-100, and zwitterionic detergents. In some embodiments, the cellular material of the cornea is removed using an enzymatic treatment. Lipases, thermolysin, galactosidases, nucleases, trypsin, endonucleases and exonucleases are used to remove the cellular material from the cornea. In some embodiments, the cellular material of the cornea is removed using physical techniques. These physical techniques include methods used to lyse, kill, and remove cells from the matrix of a tissue through the use of temperature, force and pressure, and electrical disruption. Temperature methods are often used in a rapid freeze-thaw mechanism. Temperature methods conserve the physical structure of the ECM scaffold. Pressure decellularization involves the controlled use of hydrostatic pressure at high temperatures to avoid unmonitored ice crystal formation that could damage the scaffold. Electrical disruption of the plasma membrane is another option to lyse the cellular material in the cornea.

In embodiments described herein, the lenticule can exhibit even lower immunoreactivity due to the degradation of immunogenic epitopes. This can be an important step when using xenogeneic donations. For example, two non-human epitopes that may be present in xenogeneic tissue are N-Glycolylneuraminic acid (Neu5GC) and Galactose-alpha-1,3-galactose (Alpha-Gal). These undesirable epitopes may be present not only inside or on the surface of stromal cells; a small fraction of the epitopes may be embedded in the glyco-amino-glycans (GAGs), also known as mucopolysaccharides, that wrap around ECM collagen fibrils. In certain embodiments, the epitopes can be selectively removed by enzymatic treatments, such as by galactosidase treatments, and additional washing. Alternatively, corneal tissue may be harvested from knockout transgenic animals (e.g., transgenic pigs), which lack any immunogenic epitopes, thus producing non-immunogenic lenticules without requiring a epitope degradation step.

In embodiments described herein, the decellularized lenticule can be further sterilized in conjunction with packaging and sealing. Sterilization can be accomplished using wet agents, radiation, or electron beams. In one preferred embodiment, sterilization of the decellularized lenticule is performed using UV radiation, as damage to the collagen scaffold is less likely to occur. The usage of UV radiation can be advantageous to improve the lenticule's optical transparency.

In another aspect of the invention, the shape and orientation of the lenticule are designed for optimal results. In some embodiments, the diameter of the lenticule is from about 0.5 millimeters (mm) to about 10 mm, or from about 3 mm to about 9 mm, or from about 4 mm to about 8 mm, or from about 5 mm to about 7 mm. Again, without reciting every possible sub-range between 0.5 mm and 10 mm, it should be clear that all such sub-ranges are contemplated and considered part of the invention.

The donor corneal stroma can be sliced and/or further shaped to obtain the desired shape. Cutting can be performed mechanically, e.g., with a microkeratome or the like, or by laser processing, e.g., by photo-ablation with an excimer laser or photo-cleavage with a femtosecond laser. To reduce the possibility of asymmetry, the corneal tissue segment is preferably taken from the central portion of the donor cornea, e.g., with the optical or geometric axis of the donor cornea preserved at the center of the lenticule. The shape of corneal tissue segment will be dictated by the dioptric power change needed to correct the patient's refractive error. For example, for correction of hyperopia (hypermetropia) and/or presbyopia, the goal is typically to increase the curvature of the cornea and the desired lenticule shape will be slightly convex on at least one side. In some embodiments, the maximum thickness of the lenticule will be less than 600 micrometers, less than 400 micrometers, less than 200 micrometers, less than 100 micrometers, or less than 50 micrometers. The smaller the diameter and the thinner the lenticule, the faster it will be integrated into the patient's stromal bed.

Stromal collagen fibrils are long polymeric (polypeptide) strings. They are triple-winded proteins. The length of a single collagen fibril is nearly macroscopic, and so each of the fibrils individually can be a strong scatterer of light. The fact that stroma is transparent in the axial direction is the result of negative summation of all these strongly scattering contributions. That is to say, the collagen fibrils contribute collectively, despite their individual scattering, to collective near zero scattering in total. This collective transparency is achieved if fibrils are arranged parallel in one plane. In the corneal stroma, the arrangement plane is vertical to the optical axis. This unique arrangement is present in the cornea but not observed in other organs. In other organs like intestine or myocardium membrane, ventricular valves, the fibrils are not carefully aligned and so the light is scattered. The same can be said about the eye's limbal collagen.

In addition to transparency, natural selection has optimized the structure of cornea for strength as well. Collagen fibril's length and alignment contribute substantially to in-plane (tangential) tensile (pull) strength of the stroma. The shape of the natural eye is maintained by hydrostatic intraocular pressure exerting tangential tensile (pull) stress on the stroma. The in-plane orientation of collagen fibrils lends to the cornea transparency and provides significant mechanical tensile (pull) strength. However, this strength is largely limited to in-plane exertions of force. The strength of the corneal stroma in direction of the optical axis is substantially weaker. One manifestation of this axial strength deficiency is the scaffold's swelling when immersed in water, e.g., in buffered saline solution (BSS). The swelling is almost exclusively unidirectional, in direction of the optical axis. Swelling in the in-plane direction is negligible.

This weakness of the scaffold is a source of concern, as the shape fidelity of the optically active lenticule is critical to a successful additive refractive surgery. Swelling of the scaffold in the axial direction can induce refractive errors.

The amount of swelling often is a function of the immersion fluid. The highest degree of swelling, i.e., by some 250-400% of its nominal thickness, is observed when surfactants and/or detergents are added to the water. BSS typically induces swelling by some 150-250% of nominal thickness. The swelling in alcohols (both light and heavy) is typically less. (The nominal thickness can be defined as the axial thickness of the original excised stromal segment (lamella) before the decellularization step, e.g., when the tissue specimen is very fresh, for example, less than about 60 seconds or so post-excision—or longer when the specimen retains epithelial and/or endothelial cells.)

In case of thick lenticules the swelling may cause the lenticule be so thick that it becomes difficult to place back the flap on the stromal bed. The flap may also be too short to cover the added material (raising danger of epithelial undergrowth) and may require an additional procedure of mechanical stretching and/or suturing of the flap to the stromal bed.

The unidirectional mechanical weakness of the collagen-scaffold together with changes in osmotic properties and/or the scaffold's water affinity (as compared to stroma before decellularization) can cause significant unidirectional swelling in direction of the scaffold's thickness (i.e., the axial direction).

Free water resides inside the collagenous tissue. In the intact natural cornea, the water content of the stroma is controlled by the cornea's overall structure, e.g., the epithelial and endothelial membranes that provide the cornea boundaries. However, when exogenous stromal tissue is implanted during additive refractive surgery, this balance is often perturbed, and the water content of the implanted lenticule has a tendency to increase and cause post-operative swelling beyond the nominal thickness.

According to the invention, if a flat (cylindrical) collagenous tissue specimen is placed between two plates exerting steady pressure, the fluid content can be reduced (or equivalently the collagen concentration can be increased). The same is true for a shaped lenticule that has undergone decellularization. The press should provide for the drainage such that excessive free fluid will exit sideways from the tissue. (In the case of a shaped lenticule, at least one of the plates of the press should be curved to accommodate the radial variation in the lenticule's thickness. Preferably, the pressure is applied gently for a desired time. Depending on the desired degree of compression, pressure can be exerted on the collagen scaffold for a predefined duration ranging from seconds to hours, e.g., from 30 seconds to an hour, or from 5 minutes to a half hour in some instances.

The distance travelled by the plates of the press allows calculation of the approximate collagen concentration. For example, if the nominal thickness of a flat excised tissue segment is 100 micrometers and it swells to become 200 micrometers after a decellularization process, the collagen content of the composition can be about 15%. If it were then recompressed to a 100 micrometer thickness, the nominal collagen concentration would be restored to an approximately 30% level. If the scaffold is further compressed to a 50 micrometer thickness, then the collagen concentration will be approximately 60%. If the scaffold is further compressed to a thickness of 40 micrometers, then the collagen concentration will be approximately 75%. (Collagen content percentage can measured as the weight fraction of a vacuum desiccated lenticule relative to its weight prior to desiccation when it is in full equilibrium with water.) This value is achieved only after prolonged pressure and is close to the high end of reasonably achievable collagen concentrations. Remaining water at this point is tightly bound to the proteins, e.g., by Van der Waals forces, and further pressure may compromise the integrity of the collagen fibrils.

The process of compressing collagenous tissue is largely reversible if the scaffold is removed from the press and immersed back into fluid. The scaffold re-swells to approximate its pre-compression thickness. However, in another aspect of the present invention, methods are disclosed for preventing re-swelling by strengthening of collagen scaffolds, most notably in the axial strain direction via crosslinking of the collagen scaffold during the pressing process. Compression of the scaffold, and/or removal of the excess fluid, can be also achieved by exposing the scaffold to acceleration, e.g., in a centrifuge. For example, accelerations ranging from 10 G up to 100 G (981 m/s$^2$) or more can be employed. The removal of the excess fluid can be also achieved or aided by exposure of the scaffold to vacuum or reduced pressure.

In certain embodiments, crosslinking can be achieved by a chemical agent. An external chemical molecule can be added (mostly in water solution or some other fluid) in sufficient concentration, duration, and temperature. The molecule can be constructed to bond on one end with one collagen fibril and on the other end with another collagen fibril. The type of the bond may be specific to the agent or need not be a peptide-type bond. The chemical molecule creates a physical bridge with chemical bonds (covalent bonds) as strong attachments. Sufficiently dense collections of such bridges imparts new strength and/or stiffness to the collagen scaffold in the axial direction. The collagen molecules need not to touch each other but be at a distance of approximately the agent's molecule size. This relaxed actuation requirement makes the crosslinking process easy. Examples of chemical crosslinking agents are glutaraldehyde, genipin and simple sugars.

Collagen fibrils are strong light-scatterers themselves, but their orientation and statistical arrangement collectively eliminate the scattering. A potential disadvantage of crosslinking agents and energy mediating molecules is that they introduce exogenous materials into the collagen scaffold that can act as light-scatterers and adversely affect the optical transparency of the scaffold when it is used as an implantable lenticule in an refractive correction procedure.

In other embodiments, the collagen fibrils can also be strengthened by a stable chemical bond established directly between the fibrils. This happens when the fibrils touch each other, but not spontaneously. The so-called peptide bond is endothermic and requires that external energy be delivered locally and timely to the location where the fibrils touch. In some embodiments, a specialized mediation-molecule can be employed, which receives energy from light quanta. The mediating molecule can then provide the bonding energy, or become a catalyst of the crosslinking process, without participating itself in the structure of the link. The light is thus an indirect energy source for building a stable bond. One example of a mediating molecule is riboflavin when exposed to light, e.g., from a light-emitting diode (LED) or the like.

In yet another variant method, the scaffold's collagen fibrils can be bonded directly to each other by radiation absorbed locally where fibrils touch each other. There is no need for exogenous mediating molecules to capture the quanta of energy (although endogenous molecules such as glyco-amino-glycans (GAGs) present in the collagenous tissue may provide a similar function). The quanta is absorbed directly and timely in the abutment of the touch event. This method can utilize various forms of direct irradiation e.g., visible, blue, or UV radiation, gamma rays or even electron beams. One preferred energy source is UV light having an energy density of at least 100 Joules per square centimeter, or at least 200 Joules per square centimeter, or at least 300 Joules per square centimeter. For example, a desirable energy density for the actinic radiation can range from about 100 to about 5000, or between about 200 and about 1000, or between about 300 and about 600 Joules per square centimeter.

The density (compression/compaction) of collagen scaffold can play a role in the speed of the crosslinking. If the collagen concentration is higher (i.e., the collagen scaffold is more compressed or otherwise compacted), then the process of crosslinking can proceed faster.

The critical (threshold) dosage required for pure radiation-induced crosslinking (without any mediation agents like riboflavin) alone may be a function of the decellularization process. The threshold dosage for the non-decellularized stroma can be as much as 3 to 300 times larger than that for decellularized collagen scaffold. (This ratio can also be a function of the applied radiation's wavelength.) In another aspect of the present invention, it has been discovered that the threshold for collagen crosslinking drops if decellularization removes more of the extracellular material present in stroma (like the GAGs). The differences in the threshold may vary by as much as one order of magnitude, dependent on the applied decellularization protocol, and radiation's wavelength. This crosslinking-threshold lowering appears to correlate with the intensity of the decellularization protocol.

Crosslinking can be executed concurrently with compression/compaction or in a subsequent step via a dedicated UV radiation source (or alternatively by environmental UV radiation, e.g., sunlight).

If light energy is used to induce crosslinking, the absorption of the light may be governed by Beer's Law, that is to say more light will be absorbed in the surface strata of the material where the light impinges and lesser amounts will be absorbed in the deeper strata of the material. The amount of light available to induce crosslinking essentially decays exponentially. If there are differences in the amount of light scattering molecules in the scaffold, this can also affect the distribution of energy since the scattering agents will reduce the amount of light that can pass through to underlying regions of the irradiated material. In the present invention these effects can be used advantageously to create a graded degree of crosslinking and/or impart different properties to a surface region of the scaffold that is exposed to the actinic radiation.

Thus, the natural absorption profile of light energy alone, or together with the introduction of light scattering agents (e.g., as a surface coating), offers an option of selective surface crosslinking and/or a lesser degree of crosslinking below the surface of the collagen scaffold. The selective crosslinking of a lenticule's surface can be advantageous to impart a different adhesiveness, permeability, or smoothness to the surface, or to facilitate greater or less penetration by a recipient's cells post-implantation. For example, if a scaffold is compressed to about 60% collagen density, and selectively crosslinked on the surface to depth of about 5-to-10 micrometers, the surface will retain a high density while the rest of the scaffold will remain unchanged from its expanded state following the decellularization process. Such a densified surface can provide a pseudo-Bowman's Membrane.

Moreover, surface crosslinking can be employed to impart a patterned effect to the anterior surface, posterior surface, or both, by selectively treating a portion of the surface with a light scatterer or exposing the scaffold via a patterned mask. Surface patterning can selectively alter the friction or adhesiveness of portions of the surface.

There are three methods to selectively crosslink the surface of the scaffold. First, by using short wavelength UV radiation with strong absorption in the scaffold, the penetration depth can be limited. In this approach, preferred wavelengths will range from about 230 to about 150 nanometers and more preferably from about 215 to about 193 nanometers (e.g., 193 nm). The impingement angle of radiation is typically normal to the surface but can vary from between 0 and 60 degrees to the surface normal.

Alternatively, longer wavelength UV radiation can be used, e.g., extending to about 400 nanometers, and entering the scaffold at a grazing-incidence angle greater than 60 degrees, preferably greater than 75 degrees or higher, e.g., ranging from about 80 to about 89.9 degrees. One advantage of this method is the ready availability of reliable and intense UV radiation sources at wavelengths about or above 280 nanometers due to their commercial use. The usage of laser radiation as light source can also be preferred as the spatial coherence of laser light allows for good incidence angle definition.

In yet another alternative, an evanescent wave slab waveguide can be used. This allows for very shallow crosslinking depth (about the wavelength of the incident light). For example, when using 380 nanometer UV radiation, crosslinking can be confined to a micrometer or less surface layer.

Importantly, by densifying (or selectively crosslinking more vigorously) the anterior surface of the lenticule, it will exhibit a different texture than the posterior surface because Bowman's membrane is denser and smoother due to the tightly woven collagen type I fibrils. The posterior surface (opposite the anterior surface) will be rougher due to a less dense composition of this portion of the lenticule (and the fact that it is formed by mechanical or laser cutting of the tissue). This difference in roughness can be especially advantageous when the lenticule is used for intrastromal or intracorneal implantation because it is highly desirable that the lenticule be strongly adherent to the stromal bed. If a less than optimal refractive result is observed post procedure, the flap may need to be folded back again to permit further keratoplasty (re-sculpting of the lenticule) by laser ablation or the like. Any movement of the lenticule from its original position in the stromal bed could compromise the effectiveness of this keratoplasty. Moreover, the smoothness of the anterior surface of the lenticule also makes it less likely that reopening the flap will dislodge the lenticule.

In yet another aspect of the invention, the posterior surface can be treated following excision, shaping and decellularization to make the surface more adherent to the stromal bed. For example, a crosslinking or adherence-enhancing agent can be applied, prior to sterilization and packaging. Alternatively, the crosslinking or adherence-enhancing agent can be applied by the clinician during the procedure before implantation.

In some embodiments, the harvested, shaped and decellularized lenticule will be marked in such a way that the clinician can maintain the proper orientation of the lenticule during the reopening of the flap and laser re-sculpting adjustments. The marking can be accomplished in a variety of ways, but in all instances will be invisible to the patient once the lenticule is in place in the stromal bed. In some embodiments, the marking can be a microscopic notch in the top anterior portion or the bottom anterior portion of the lenticule. In some embodiments, the marking can be a line or dot made with a dye placed at the top anterior or bottom anterior of the lenticule.

Also disclosed herein are methods of forming a lenticule from donor stroma. In some embodiments, a method of forming a lenticule from donor stroma comprises removing a portion of stroma from a central region of a donor cornea and shaping a posterior surface of said donor stroma to provide a lenticule body of a desired shape. To reduce the possibility of asymmetry, the tissue segment is preferably taken from the central portion of the donor cornea, e.g., with the optical or geometric axis of the donor cornea preserved at the center of the lenticule. The shape of tissue segment will be dictated by the dioptric power change needed to correct the patient's refractive error. For example, for correction of hyperopia (hypermetropia) and/or presbyopia, the goal is typically to increase the curvature of the cornea and the desired lenticule shape will be slightly convex on at least one side. The lenticule can also include one or more asymmetrical markers (like the letter "L") on the perimeter of the lenticule to identify the lenticule's anterior and posterior surfaces.

The scaffolds of the present invention can further provide an advantage as refractive (e.g., additive) lenticules in that they can be designed to have a higher refractive index than native stromal tissue. At present, use of implanted lenticules to alter the curvature of the cornea is typically limited to a total dioptric power (e.g., the sum of the dioptric values of the native cornea and the additive lenticule) of less than about 50 D (as measurable in the vicinity of the apex), before epithelial instability or unacceptable epithelial erosion occurs. Implantable scaffolds with higher indices of refraction afford the possibility of higher hyperopic corrections. The standard refractive index of stromal tissue is typically about 1.376. The compression/compaction techniques of the present invention can provide scaffolds with refractive indices greater than 1.377, greater than 1.378, greater than 1.379, greater than 1.38 or higher. Gradients in the lenticule's refractive index can also be achieved by controlled crosslinking. (Such gradients can also be utilized for correction of higher order refractive errors, the terms of which can be described by higher order Zernike polynomials of human eye.)

In embodiments described herein, the methods produce a lenticule with a shape and density designed for optimal results. The lenticules are obtained by first cutting a disc-shaped tissue segment from donor stroma in a manner that preserves the Bowman's membrane as the anterior surface. In some embodiments, the diameter of the lenticule is from about 0.5 mm to about 10 mm, from about 3 mm to about 9 mm, from about 4 mm to about 8 mm and from about 5 mm to about 7 mm. The tissue segment can be sliced and/or further shaped or cut in such a manner that the desired shape is obtained during the slicing procedure. Cutting can be performed mechanically, e.g., with a microkeratome or the like, by laser processing, e.g., by photo-cleavage with a femtosecond laser. Cutting may be performed, for example, with instruments such as those disclosed in International Patent Application No. PCT/IB2016/054793, entitled "Surgical Apparatus and Blade Elements for slicing Lamellar Segments From Biological Tissue," herein incorporated in its entirety by reference.

Lenticules can also be obtained by femtosecond laser ablation, excimer laser ablation, or by cutting with the water jet. If preservation of the anterior segment is not necessary, lenticules can also be obtained by Small Incision Lenticule Extraction (SMILE) techniques, disclosed for example in U.S. Pat. No. 6,110,166 entitle "Method For Corneal Laser Surgery," also herein incorporated in its entirety by reference.

In embodiments described herein, the maximum thickness of the lenticule will be less than 600 micrometers, less than 400 micrometers, less than 200 micrometers, or less than 100 micrometers, or less than 50 micrometers. The smaller the diameter and the thinner the lenticule, the faster it can be integrated into the patient's stromal bed.

In certain embodiments, the donor stroma is decellularized to produce lenticules with reduced potential for adverse reaction on the part of the patient to immunogens of cellular origin. The decellularized lenticules produced using the methods of the present invention are between 90 percent to 100 percent, or preferably between 95 percent to 99.99 percent, or between 98 and 99.9 percent, free of cells and/or cellular remnants. (Only about 2 percent of the typical cornea is composed of cells. The other 98 percent is largely extracellular matrix (ECM), primarily collagen, water, GAGs and proteoglycans. The preferred and mostly practiced method to characterize the amount of cellular remnants after the decellularization process is based on detection of DNA or alternatively RNA residues. These methods are very sensitive and of high specificity. These measurements are typically normalized to the amount of DNA/RNA present in lenticule before the decellularization step. Without reciting every possible sub-range between 90% and 99.99%, it should be clear that all such sub-ranges are contemplated and considered part of the invention. For example, the lenticules produced can be 90%, 95%, 99% to 99.7%, 99.7% to 99.9%, or better, free of native cellular materials (as measured by DNA/RNA residual content). In other words, the amount of cellular material remaining in the lenticule, as measured by residual DNA or RNA content, can be less than one percent, or less than 0.1 percent, or less than 0.01 percent by weight of the original DNA or RNA content. (A significant amount of decellularization can occur by virtue of the lenticule extraction itself. As much as 95 percent of the total corneal cellular content resides in the epithelium and the endothelium, which can be mechanically discarded leaving only corneal stroma for the further decellularization.)

The removal of cellular material from the donor stroma (decellularization) can be accomplished using a variety of techniques. In one preferred embodiment, the cellular material of the cornea is removed by chemical treatment. The chemicals used to lyse and remove cells from the cornea can include acids, bases, surfactants (e.g. sodium tetradecyl sulfate (STS)), ionic detergents (e.g., sodium dodecyl sulfate (SDS)), non-ionic detergents (e.g., Triton X-100), and zwitterionic detergents.

Alternatively or in addition, the cellular material of the cornea can be removed using an enzymatic treatment. Lipases, thermolysin, galactosidases, nucleases, trypsin, endonucleases and exonucleases can be used to remove the cellular material from the cornea. In some embodiments, the cellular material of the cornea is removed using physical techniques. These physical techniques include methods used to lyse, kill, and remove cells from the matrix of a tissue through the use of temperature, pressure, and/or electrical disruption. Temperature-based decellularization methods can include rapid freeze-thaw protocols. Such temperature-based methods conserve the physical structure of the ECM scaffold. Pressure decellularization involves the controlled use of hydrostatic pressure at high temperatures to avoid unmonitored ice crystal formation that could damage the scaffold. Electrical disruption of the plasma membrane is another option to lyse the cellular material in the cornea.

In some embodiments, the lenticule can be further treated to exhibit even lower immunoreactivity due to the degradation of immunogenic epitopes. This is an important step when using xenogeneic donations. For example, two non-human epitopes that may be present in xenograft tissue are N-Glycolylneuraminic acid (Neu5GC) and Galactose-alpha-1,3-galactose (Alpha-Gal). These undesirable epitopes are present not only inside or on the surface of stromal cells; a small fraction of the epitopes may be embedded in the glyco-amino-glycans (GAGs), also known as mucopolysaccharides, that wrap around ECM collagen fibrils. In certain embodiments, such epitopes can be removed or conformationally altered (to neutralize the immunogens) by enzymatic treatments, such as kinase or galactosidase treatments, and additional washing. Alternatively, corneal tissue may be harvested from knockout transgenic pigs which lack epitopes, thus producing non-immunogenic lenticules without requiring a degradation step. In some instances, it can also be preferable to remove epithelial and/or endothelial cell layers or residues from the lenticule prior to epitope neutralization. This can be accomplished by scraping, e.g., with a scalpel, or by rubbing, e.g. with an abrasive material of suitable roughness.

In embodiments described herein, the methods of producing decellularized lenticules can further include a sterilization step, which may be in conjunction with packaging and sealing. Sterilization can be accomplished using wet agents, gamma radiation, or electron beams. In one embodiment, sterilization of the decellularized lenticule is performed using an electron beam, as damage to the collagen scaffold is less likely to occur. Alternatively, the radiation utilized to induce crosslinking can also provide sufficient energy for sterilization of the lenticule.

In some embodiments, the preparation of the harvested, shaped and decellularized lenticule will include a step of marking the lenticule in such a way that the clinician can maintain the proper orientation of the lenticule during the reopening of the flap and laser adjustments. The marking can be done in a variety of ways, but in all instances will be invisible to the patient once the lenticule is in place. In some embodiments, the marking can be a microscopic notch in the top anterior portion or the bottom anterior portion of the lenticule. In some embodiments, the marking can be a line or dot made with a dye placed at the top anterior or bottom anterior of the lenticule. These methods can also include engraving one or more asymmetrical markers (like the letter "L") on the perimeter of the lenticule to identify the lenticule's anterior and posterior surfaces.

This invention and embodiments illustrating the method and materials used may be further understood by reference to the following exemplary protocol. Corneal tissue can be harvested from a porcine donor. The lenticule can be taken from an area within the donor stroma as to maintain the high density of collagen type I fibrils or Bowman's membrane at the anterior surface of the lenticule and a less dense posterior surface. Alternatively, the corneal tissue can be taken from a stromal region beneath the naturally densified surface.

As shown in FIG. 1A, a target region of the donor cornea can be cut into a disc-shaped lenticule 10A, having an anterior surface 12, a posterior surface 14 and organized layers of collagen fibrils 16. At this stage, the lenticule will typically have a diameter of about 0.5 to 10 millimeters and a thickness of less than 250 micrometers.

Figure 1B:
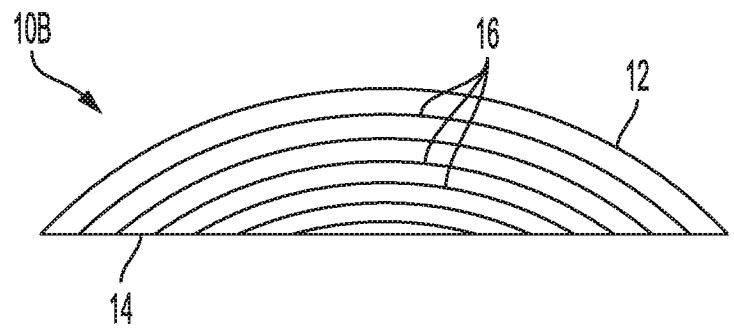
FIG. 1B is a schematic, cross-sectional illustration of an excised stromal tissue segment following decellularization, showing swelling of the tissue and consequent separation of collagen fibrils.

FIG. 1B shows a lenticule following decellularization, e.g., by chemical treatment, enzymatic treatment or physical techniques, to produce a lenticule which is 95-99.99% free of cellular material. If desired, the decellularized, shaped lenticule can be further treated to degrade immunogenic epitopes. The lenticule can further be washed and sterilized and, if desired, a crosslinking agent applied to the anterior and/or posterior surface of the lenticule. The decellularized lenticule (typically swollen due to the application of detergents, surfactants and/or washing solutions) exhibits greater separation of the fibril layers 16. In some embodiments, the top anterior surface of the lenticule can also be marked with a notch to assist in lenticular orientation in the patient's stromal bed.

Figure 1C:
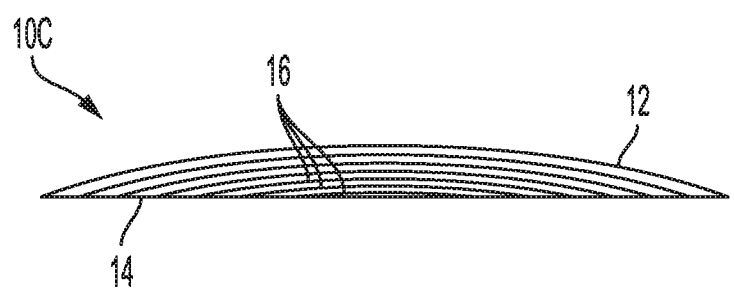
FIG. 1C is a schematic, cross-sectional illustration of an excised stromal tissue segment following decellularization, compression/compaction and crosslinking according to the invention.

In FIG. 1C, the decellularized (and potentially swollen) lenticule is then subjected to compression in order to drive excess fluids from the lenticule body and increase the collagen density. The collagen fibril layers are compressed together and then at least partially crosslinked to inhibit subsequent swelling.

Figure 2:
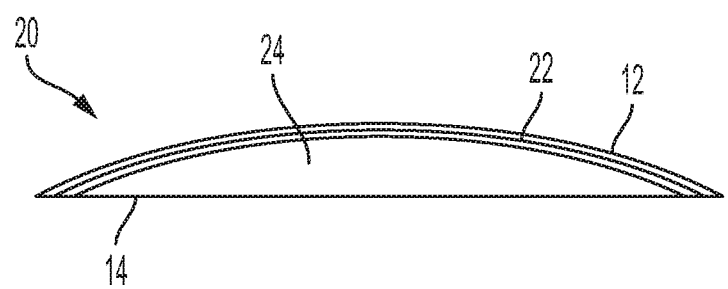
FIG. 2 is a schematic, cross-sectional illustration of an excised stromal tissue segment following decellularization, compression/compaction and selective crosslinking of the anterior surface region.

In FIG. 2, a lenticule 20 is shown having an anterior surface region 22 in which the collagen fibril layers have been compressed/compacted and crosslinked. The bulk region 24 of the lenticule 20 can also be crosslinked to inhibit swelling but not to the same degree as the anterior surface region 22.

Figure 3:
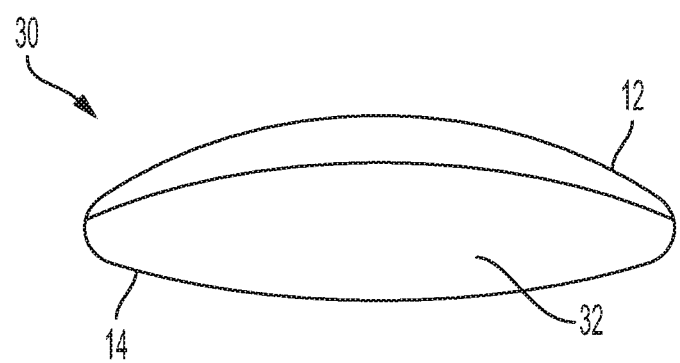
FIG. 3 is a schematic, cross-sectional illustration of an excised stromal tissue segment following decellularization, compression/compaction and selective patterning of a posterior surface region.

In FIG. 3, a lenticule 30 is shown in which one surface (e.g., the posterior surface 14) has been formed with a pattern 32 to promote post-operative integration. The pattern 32 can be formed by selective application of agents, selective irradiation or a combination of these techniques. (It should be clear that the pattern can be applied to the anterior surface 12, the posterior surface 14, or both surfaces.)

Figure 4A:
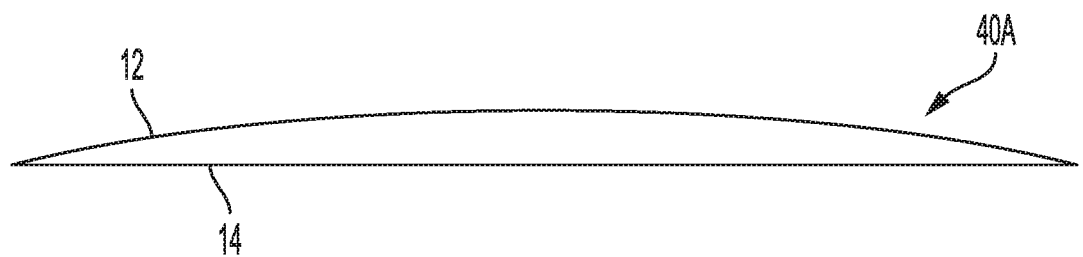
FIG. 4A illustrated a lenticule according to the disclosure in flattened shape, which is the typical shape during manufacturing and/or transport.

FIG. 4A illustrated a lenticule 40A according to the disclosure in flattened shape, which is often a typical shape during manufacturing and/or transport.

Figure 4B:
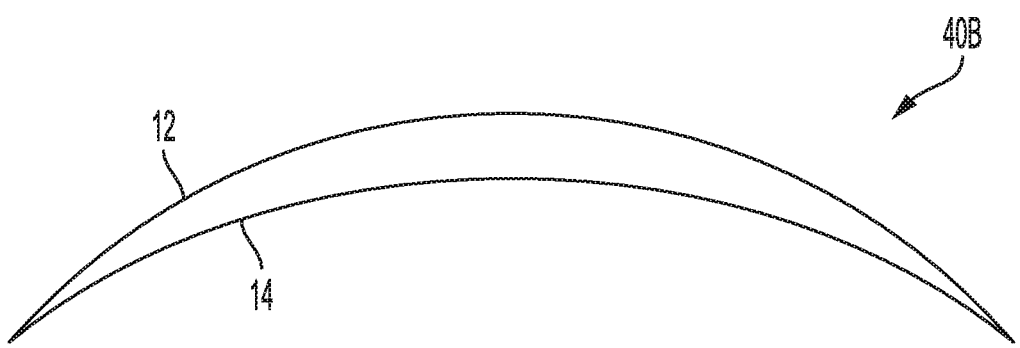
FIG. 4B illustrates a lenticule in a final curved state as prepared for intracorneal implantation.

FIG. 4B illustrates a lenticule 40B in an exemplary final curved state for intracorneal implantation. The lenticules can take various shapes for correction of different refractive errors or ocular conditions (discussed further below). Although the lenticules are generally illustrated as spherical or spheroidal in shape, it should be clear they can likewise be ellipsoidal or any desired shape (e.g., partially toroidal). Such shapes can be useful in correcting astigmatisms or higher-order aberrations in a patient's vision. Such aspherical shapes can also be useful in matching the shape of the patient's cornel or limbus.

Figure 5A:
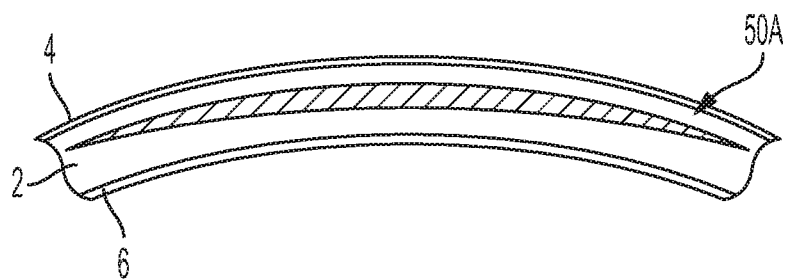
FIG. 5A illustrates a lenticule designed for intracorneal implantation to correct a hyperopic condition.
Figure 5B:
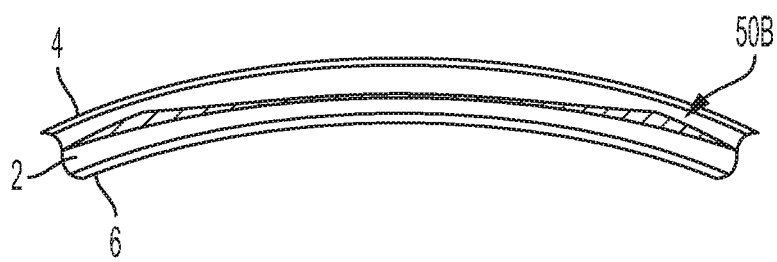
FIG. 5B illustrates a lenticule designed for intracorneal implantation to correct a myopic condition.
Figure 5C:
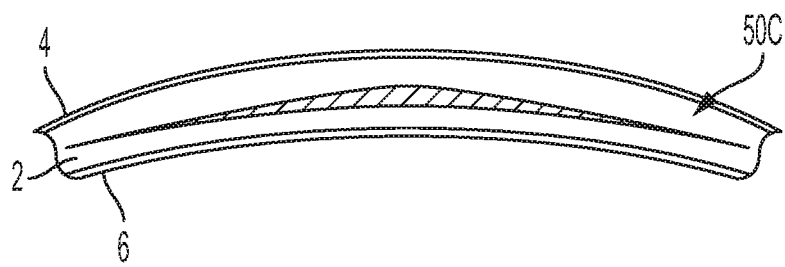
FIG. 5C illustrates a lenticule designed for intracorneal implantation to correct a presbyopic condition.
Figure 5D:
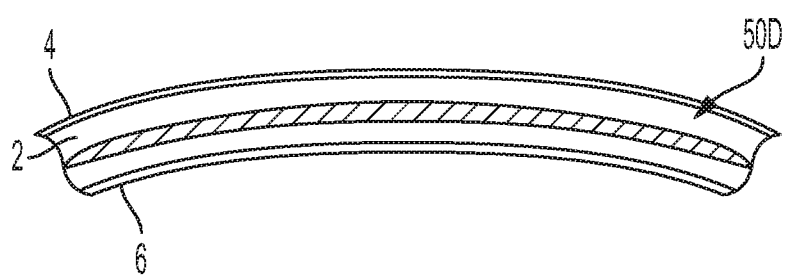
FIG. 5D illustrates a lenticule designed for intracorneal implantation to correct a condition known as keratoconus.

FIG. 5A illustrates a lenticule 50A designed for intracorneal implantation to correct a hyperopic condition. FIG. 5B illustrates a lenticule 50B designed for intracorneal implantation to correct a myopic condition. FIG. 5C illustrates a lenticule 50C designed for intracorneal implantation to correct a presbyopic condition. FIG. 5D illustrates a lenticule 50D designed for intracorneal implantation to correct a condition known as keratoconus, in which the natural collagenous structure of cornea is weakened due to injury, heredity or other eye conditions, e.g., an imbalance in enzymatic or signaling activities within the cornea. The lenticules 50A, 50B, 50C and 50D are typically designed for intrastromal (between layers of natural stroma) implantation within the cornea. By placing the lenticule within the stromal tissue 2, the epithelial region 4 and endothelial region 6 are preserved.

Figure 6A:
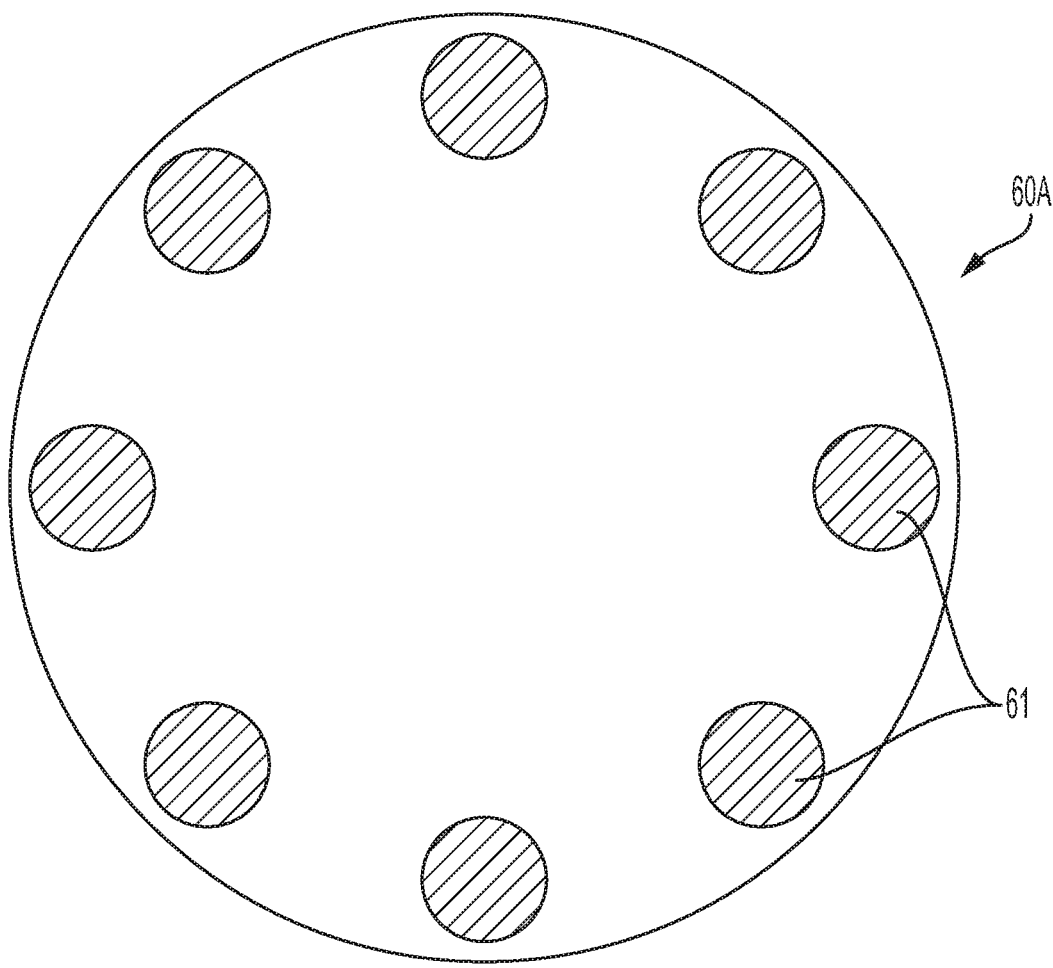
FIG. 6A illustrates another embodiment of a lenticule that is manufactured with localized spots of strong crosslinking.

FIG. 6A illustrates another embodiment of a lenticule in which the lenticule 60A is manufactured with localized spots 61 of strong crosslinking to provide areas of additional mechanical strength, e.g., for attachment of surgical stitches during penetrating keratoplasty (PK) or deep anterior lamellar keratoplasty (DALK), as discussed in more detail below.

Figure 6B:
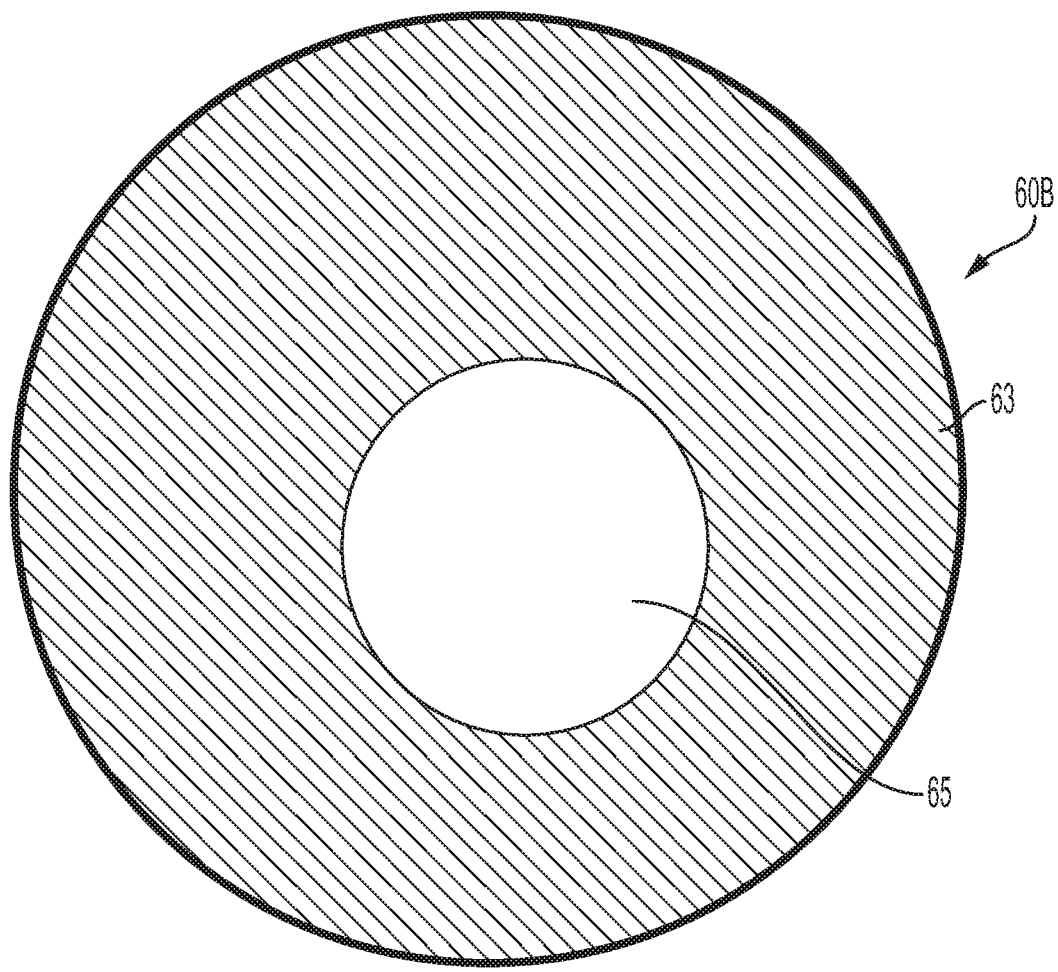
FIG. 6B illustrates yet another embodiment of a lenticule that includes a central optically active zone with moderate crosslinking and an outer or peripheral zone with strong crosslinking.

FIG. 6B illustrates yet another embodiment of a lenticule. In this embodiment the lenticule 60B includes a central optically active zone 65 (e.g., having a major diametric dimension of about 3 to 6.5 millimeters) with moderate crosslinking and an outer or perimeter zone 63 with strong crosslinking, again to provide a region of additional mechanical strength, e.g., for attachment of surgical stitches or in support of kertoconically weakened stroma outside of the visual zone. It should be noted that zones 63 and 65 need not be concentric and in instances, e.g., treatment of keratoconus, it can be desirable to offset the optically active zone from the center of the lenticule.

Figure 7A:
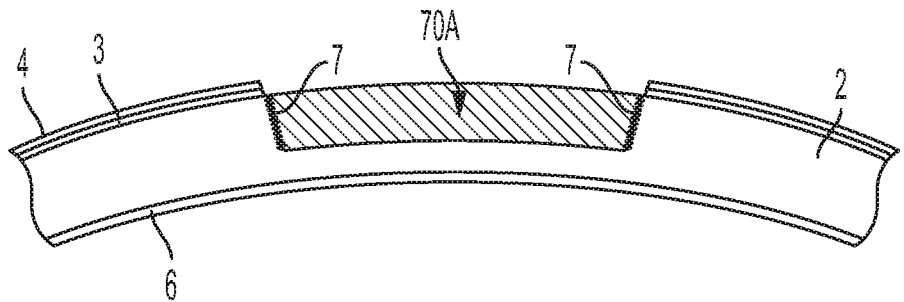
FIG. 7A illustrates the use of a lenticule for deep anterior lamellar keratoplasty (DALK)

FIG. 7A illustrates the use of a lenticule 70A according to the disclosure for a different type of intracorneal implantation, namely deep anterior lamellar keratoplasty (DALK). In this procedure, an anterior segment of the eye is first removed and the lenticule 70 is placed into the eye to replace the native Bowman's membrane 3 and a portion of the stroma 2. The lenticule 70A can initially be fixed in place by stitches 7. Optionally, the lenticule 70A can formed from native donor tissue with an intact Bowman's membrane that is preserved thorough the decellularization and compression steps of lenticule formation. Alternatively, the anterior surface of the lenticule can be selectively treated, e.g., by shallow radiative crosslinking to form a Bowman's membrane-like structure. In either case, following intracorneal implantation, the patient's peripheral epithelium can grow over the anterior surface of the implanted lenticule.

Figure 7B:
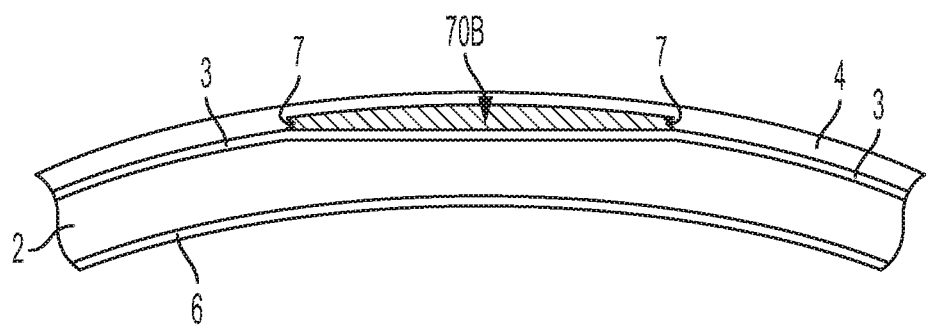
FIG. 7B illustrates the use of a lenticule configured for placement on top of the patient's intact Bowman's membrane.

FIG. 7B illustrates the use of a lenticule 70B, which is similar to the DALK lenticule shown in FIG. 7A but is typically thinner (e.g., less than 200 micrometers) and configured for placement on top of the patient's intact Bowman's membrane 3 but under the epithelium 4. In this procedure, sometimes referred to as "epikeratoplasty," lenticule 70B can again be fixed in place by stitches 7.

Figure 7C:
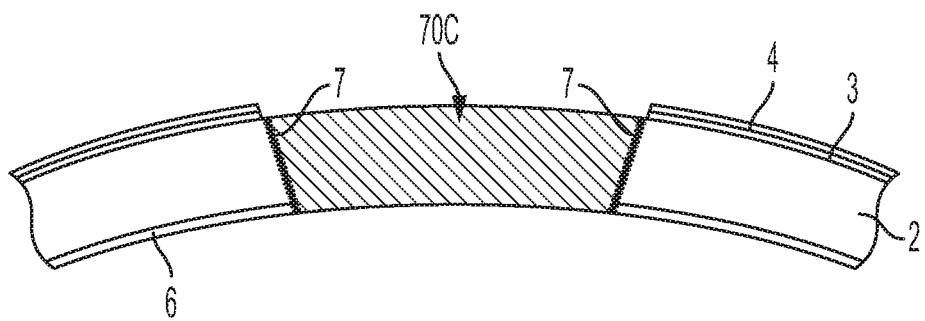
FIG. 7C illustrates yet another embodiment of a lenticule for penetrating keratoplasty (PK) procedures.

FIG. 7C illustrates yet another embodiment of a lenticule 70C according to the disclosure, in this case designed for penetrating keratoplasty (PK) procedures. Lenticule 70C is similar to the to the DALK lenticule shown in FIG. 7A but is configured to completely replace the full depth of the central corneal tissue i.e., the endothelium 6 at the posterior of the cornea, the stroma 2 and Bowman's membrane 3. Lenticule 70C can again be fixed in place by stitches 7. Following intracorneal implantation of the lenticule 70C, the patient's peripheral epithelium can grow over the anterior surface of the implanted lenticule.

Figure 8A:
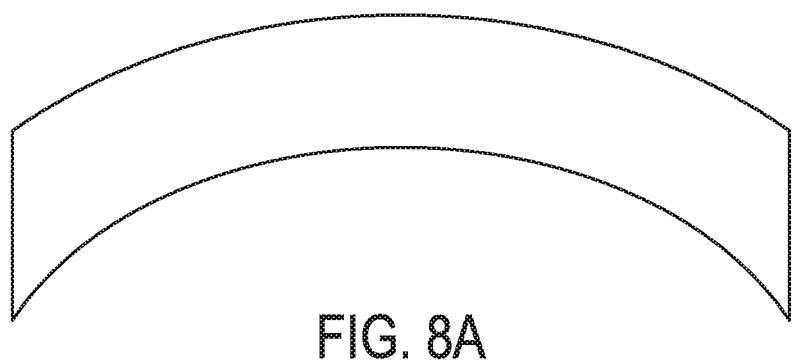
FIGS. 8A and 8B illustrate two alternate designs for the periphery of thick lenticules.
Figure 8B:
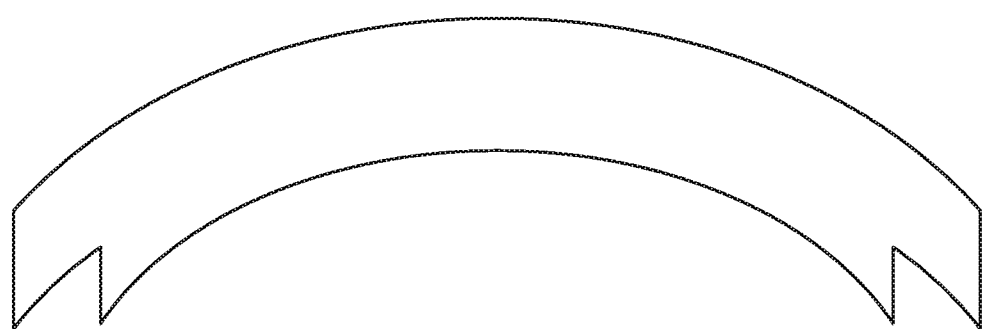
Figure 8C:
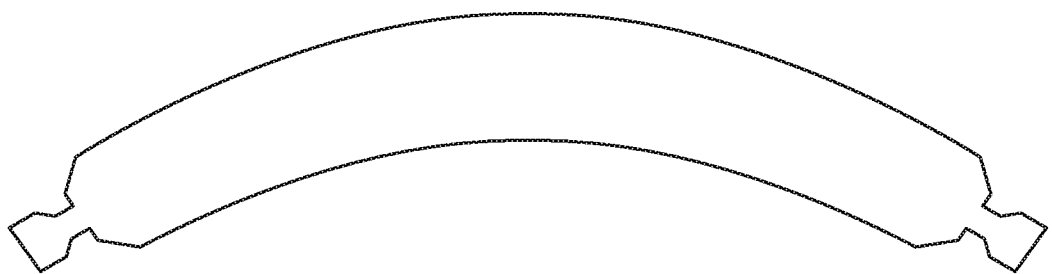
FIG. 8C shows a lenticule with a "lock and key" edge at its periphery.

FIGS. 8A, 8B and 8C illustrate two alternate designs for the periphery of thick lenticules, e.g., such as those useful in DALK and PK procedures. In FIG. 8A, a lenticule 80A is shown with a simple, e.g., cylindrical or conical peripheral edge. In FIG. 8B, a lenticule 80B is shown with a zig-zag or step-shaped edge at its periphery. The shaped edge can be designed to mate with a complementary structure formed in the native cornea to further assist in joinder of the lenticule 80B to the remaining native corneal tissue. Variations in the step shape (e.g., reverse zig-zag) can also be employed. As shown in FIG. 8C, even more advanced shape of peripheral edge can be employed to allow for mechanical latch-in or lock-in into the native cornea. The lock-in feature can reduce or eliminate need for surgical stitches along the latch-in edge in some instances. The periphery of such lenticule can be crosslinked stronger than the central part.

In some instances, the thickness of these thick lenticules can vary from the center to the edge. For example, the thickness of the lenticules can vary from about 400 micrometers at the center to 550 micrometers at the peripheral edge. This is consistent with the natural thickness variation found in most corneas where a typical intact cornea can exhibit a central cornea thickness of about 500 micrometers while the peripheral segments of the cornea can exhibit a thickness on the order of 550- to about 650 micrometers.

Figure 9:
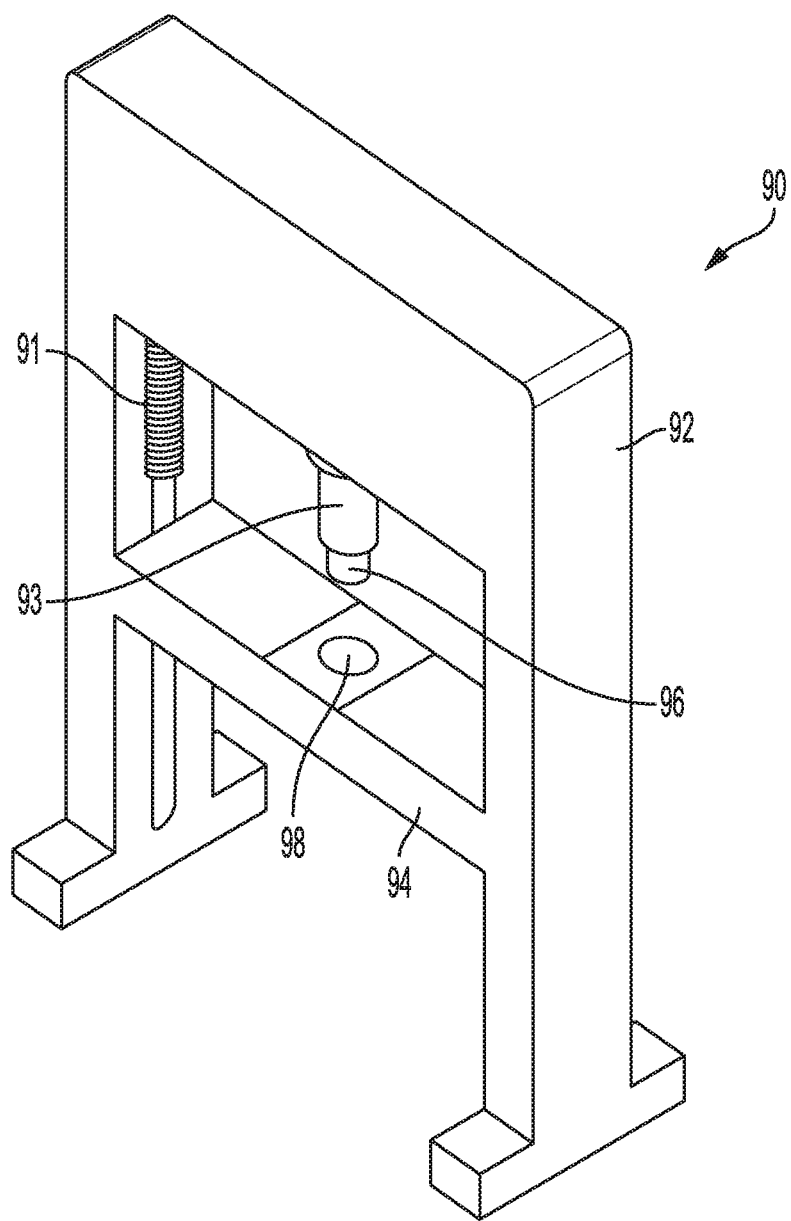
FIG. 9 is a schematic, perspective view of a press apparatus for use in compressing and crosslinking collagen scaffolds according to the invention.

FIG. 9 schematically illustrates a press 90 for use in compressing collagen scaffolds according to the invention. Press 90 can include a frame 92 and a movable stage 94. The frame holds a top press element 96 and the stage holds a bottom press element 98. At least one of these element is non-planar and shaped to conform to the desired final shape of the scaffold. Elements 96 and 98 can be brought into compression by application of a motive force (illustrated schematically by worm screw 91). In certain embodiments at least one of the press elements 96, 98 can be transparent such that a scaffold held in compression therebetween can be irradiated e.g., by UV radiation source 93, at the same time as it is being molded.

Figure 10A:
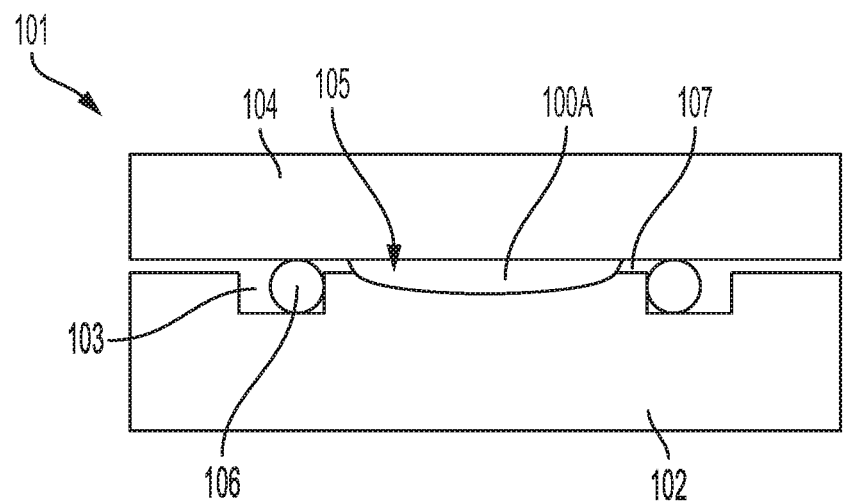
FIGS. 10A and 10B illustrate a two-part hermetically sealable compression and storage mold according to the invention.
Figure 10B:
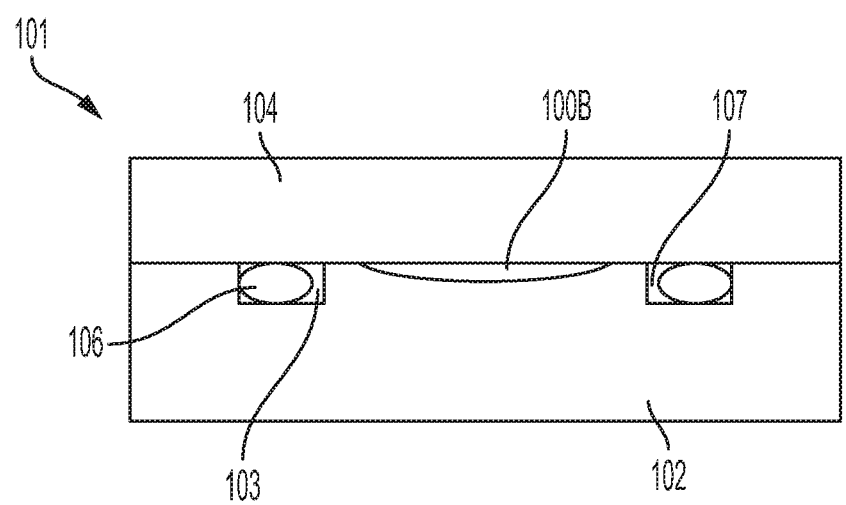

FIGS. 10A and 10B illustrate a two-part hermetically sealable compression and storage container or mold 101 according to the invention. The container/mold 101 can comprise a mold base 102 and a mold top 104 defining a chamber 105 therebetween. The purpose of the mold 101 is to compress a scaffold 100A, e.g. a decellularized stromal collagenous (extra cellular matrix) scaffold, and at the same time remove fluid from the scaffold. FIG. 10A illustrates the mold 101 in its pre-compressed state. A seal 106, e.g., an O-ring or flat gasket seal, initially separates the mold top 104 and mold bottom 102. In some instances, it can also be desirable to fill the rest of the chamber 105 not occupied by the scaffold 100A with a fluid 107 to avoid gas entrapment in the scaffold during compression. The seal 106 is adapted to accommodate fluid driven from scaffold as well as any fluid initially surrounding the scaffold in the chamber 101. In FIG. 5A, the mold is shown before the compression, but in the first moment when the seal 106 creates isolation from the ambient environment.

The top portion 104 of the mold can be at least partially transparent or translucent to allow actinic radiation to pass through to the scaffold in order to crosslink the scaffold. Alternatively, or in addition, the mold bottom 102 can be transparent to the actinic radiation. The transparent portion of the mold can be made of plastic, glass, ceramic or metal or any combination of such materials so long as it is sufficiently transparent or translucent to permit radiation transmission.

FIG. 10B illustrates the mold 101 after the compression of the scaffold 100B. The seal, e.g., an O-ring, 106 can migrate in the grove 103 such that the groove accommodates the expelled fluids. (Various other drainage mechanisms can also be employed.) In this condition, the mold 101 can be used for crosslinking and sterilization. Such sterilization can occur simultaneously with crosslinking if the appropriate wavelength and fluence of radiation is chosen. (In many instances, the dosage of radiation necessary for devitalization of viruses will be much less than that necessary for crosslinking.) The compressed, sterilized mold can further be used for shipping or long term storage. For actinic crosslinking radiation, e.g., UV radiation, to also be effective for sterilization purposes, the radiation should reach all surfaces of lenticule during this process. It can, therefore, be desirable to employ seals (e.g., O-rings or flat gaskets that are transmissive to the chosen actinic radiation. For example, if UV light is used to both crosslink and sterilize the lenticule during molding, the seal can be made from a UV transmissive or translucent material, such as a fluoropolymer, e.g., polytetrafluoroethylene (PTFE), fluorinated ethylene propylene (FEP), ethylene tetrafluoroethylene (ETFE) or perfluoroalkoxy (PFA) compositions.

The shape of the scaffold or lenticule before the compression and the matching shape of the mold will typically ensure that the density of lenticule remains homogeneous after the compression. For example, compression can reduce the vertical dimension by half and homogeneously increase the density by a factor of two.

FIGS. 10C-10F illustrate an alternative process and apparatus for compression/compaction in which the lenticules are first treated to remove water and then shaped by controlled rehydration. An excised tissue portion can be initially shaped and decellularized by any of the above-described methods. The resulting scaffold is then at least partially desiccated. The desiccation can be achieved either through chemical processes, like ethanol fluid exchange, or physical processes like drying, vacuum lyophilization, or freeze-drying, e.g., by exposure to sublimating solid $CO_2$ in a drying apparatus. The desiccation can be partial, so long as the thickness of the lenticule is sufficiently reduced such that it can fit into a mold, such as the illustrated mold 201.

Figure 10C:
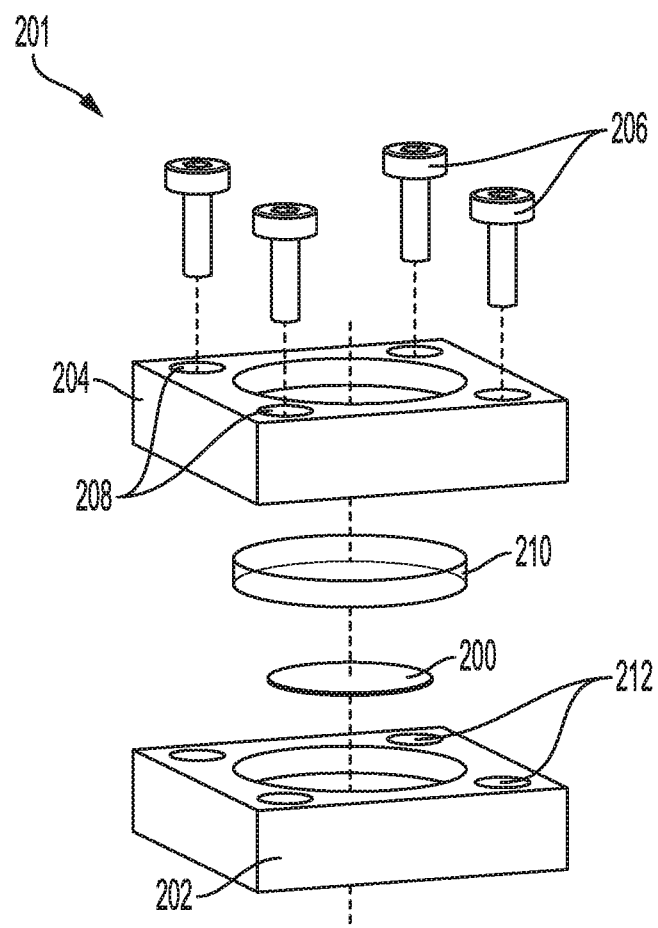
FIG. 10C illustrates an exploded view of an alternative mold for compression/compaction of scaffolds.

FIG. 10C illustrates an exploded view of mold 201, which can comprise a base portion 202 and a top portion 204, which are designed to mate with each other and define a chamber 216 therebetween. If the base and top portions of the mold are not transparent to crosslinking radiation, a radiation transparent window 210 can also be included as part of the mold 201 and forms a part of the chamber 216. The chamber 216 is larger than desiccated lenticule that will be placed within it. The shape of the chamber 216 defines a desired shape of the lenticule or scaffold, following rehydration. The chamber can impart a curved shape to the lenticule (e.g., concave, convex, planoconcave, planoconvex, astigmatic or other complex configurations). By proper design of the chamber 216, lenticules can be shaped for refractive treatments of myopia, hyperopia, or presbyopia, with or without astigmatism correction. Custom chamber shapes can be devised to treat more complicated medical conditions such as, for example, keratoconus or post-LASIK ectasia. Alternatively, the chamber can be substantial uniform in thickness if desired result is a flat or plate-like lenticule.

As shown in FIGS. 10C-10F, the top and base portions can be secured together, for example, by screws 206, which pass through holes 208 in the top portion 204 and are received by threaded screw receptacles 212 in the base portion 202. In should be clear that various other mechanisms can be used to join the base portion 202 and top portion 204 (and optional window 210) together. For example, the mold can be formed by a base portion and a threaded top portion or hinged top portion. The designation of one portion of the mold as a "base" portion and another as a "top" portion is merely for simplicity of description and does not connote any required orientation.

Figure 10D:
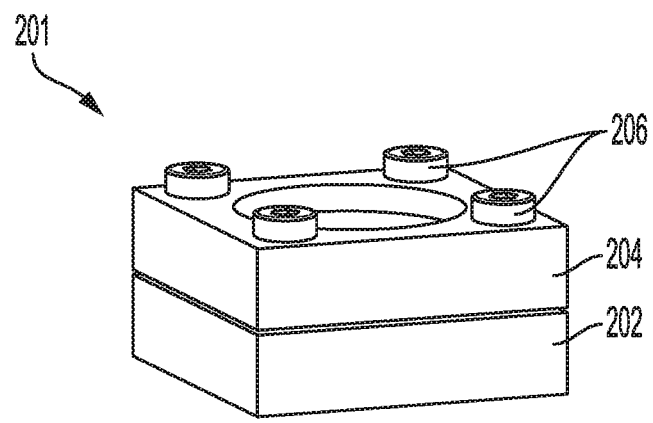
FIG. 10D shows the mold of FIG. 10C in assembled form.
Figure 10E:
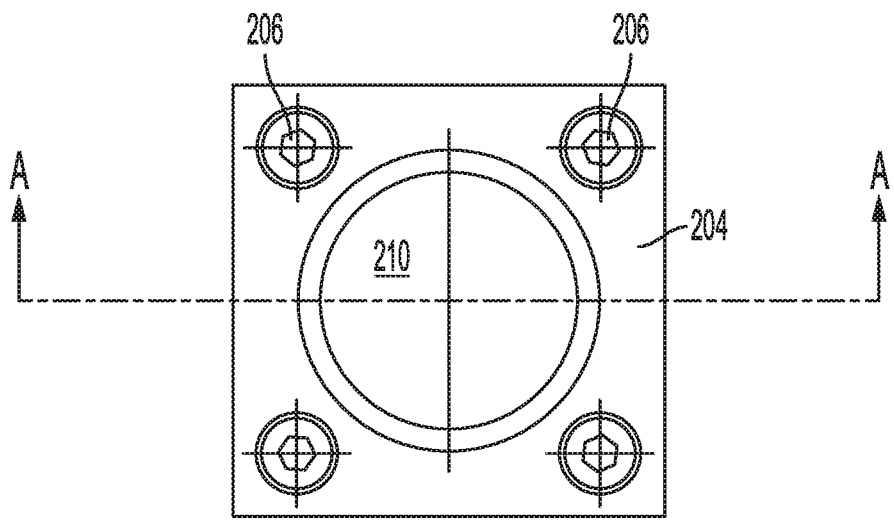
FIG. 10E is a top view of the mold of FIG. 10D.

FIG. 10D illustrates the mold 201 in its closed configuration. FIG. 10E is a top view of the closed mold 201 and also shows window 210, through which actinic radiation can pass to induce crosslinking of the lenticule.

Figure 10F:
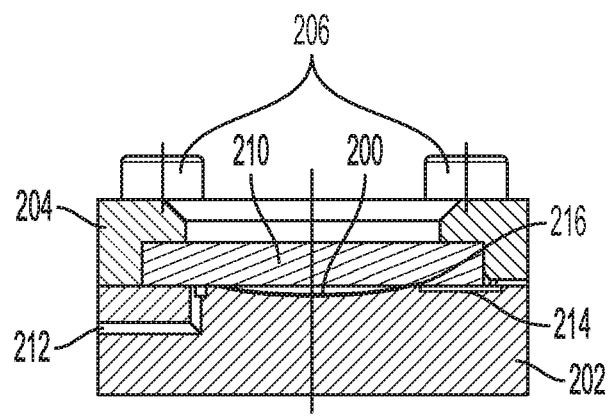
FIG. 10F is a cross-sectional view of the mold of FIGS. 10C-10E.

As shown in the cross-sectional view of FIG. 10F, a desiccated lenticule 200 can be loaded into the chamber 216 the mold 201. Mold 201 is then closed to confine the shape of the lenticule during the swelling. While constrained in the mold, lenticule is flooded by a fluid (e.g., by water, alcohol, mix of water and alcohol or heavy alcohol, or other fluids) via fluid injection channel 212 so that the lenticule 200 can swell and take shape of the static mold 201. The mold can also have one or more egress channels 214 to remove excess fluid or vent gas from the chamber as it is filled and the lenticule swells to assume the shape of the chamber.

The rehydration of the lenticule can take place slowly (e.g., over several minutes or even days) and can be aided by intermittent or constant physical shaking of the mold, or by application of acoustic energy (e.g., by ultrasound), to allow for the lenticule to assume its desired shape while globally minimizing internal tensions.

Upon rehydration, the lenticule can be crosslinked by any of the techniques described above. In the illustrated embodiment, the mold has one radiation transmitting window (e.g., formed from sapphire or other suitable material if UV radiation is used) for the crosslinking step. Alternatively, windows on both sides of the mold can be employed to offer radiative access from either or both directions.

Figure 11:
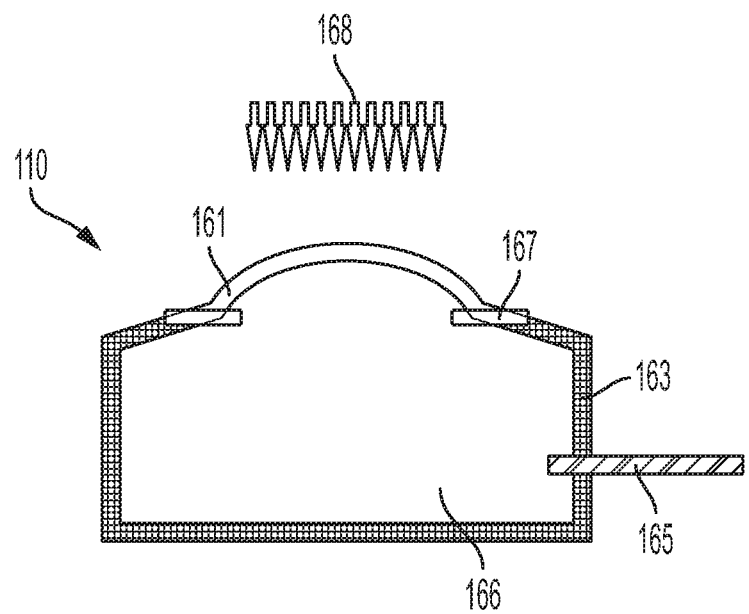
FIG. 11 illustrates a further apparatus according to the invention for stretching a scaffold.

FIG. 11 illustrates a further apparatus 110 according to the invention for stretching a scaffold 161, which can be a native decellularized stromal excision or scaffold that has been decellularized and undergone an initial compressive treatment. In this embodiment, the scaffold 161 has been attached to an open mouth of chamber 163, by sealing mechanism 167, e.g., by crimping the peripheral edge of the scaffold 161 between two flat flanges. (Various other sealing mechanisms can be employed in lieu of, or in addition to, crimping to provide a fluid-tight connection between the scaffold and the chamber mouth.) A fluid 166 is then introduced into the chamber 163 via controlled pressure conduit 165 to fill the interior of the chamber and exert pressure on the scaffold 161. For example, a horizontal and/or tangential stretching can be obtained by maintaining sufficient hydro static pressure in the chamber, for example, a pressure from about 30 to about 500 mbar, preferably from about 50 to about 200 mbar (or from about 22.5 to about 375 Torr, preferably from about 37.5 to about 150 Torr).

The application of this fluidic pressure can also cause the scaffold to de-swell (release free water), even if the fluid applying the mechanical stress to the scaffold is pure water or a balanced salt solution (BSS). Fluid can flow out of the scaffold in any direction (e.g., migration into the pressurized fluid chamber or by exudation from the outer surface of the scaffold or both). Hypertonic or hypotonic solutions can also be employed in the chamber 163 to enhance or limit this effect.

By exposing the ECM-scaffold to this type of stretching, the collagen fibrils can be aligned to build a curved shape. When a desired curvature is obtained, the shape can be preserved (or fixed) by crosslinking, e.g., by actinic radiation 168, as shown.

Figure 12:
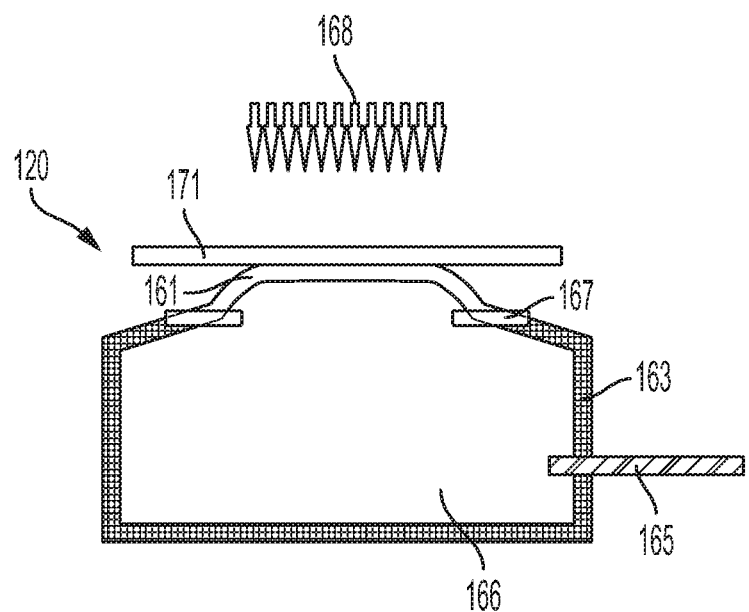
FIG. 12 shows yet another alternative apparatus, similar to the apparatus of FIG. 11 but with the addition of a compression-exerting plate element for simultaneous stretching of the scaffold and compressing it, as well as for facilitating exposure to crosslinking radiation.

In FIG. 12, yet another alternative apparatus 120 is shown, similar to the apparatus of FIG. 6 but with the addition of a compression-exerting plate element 171 for simultaneous stretching and compressing of the scaffold, as well as for facilitating exposure to crosslinking radiation. The horizontal and/or tangential stretching is again provided by maintaining sufficient hydrostatic pressure in the chamber about 30 to about 500 mbar, preferably from about 50 to about 200 mbar. The vertical/radial compression can be applied simultaneously by top plate 171. Preferably, the top plate 171 is at least partially transparent e.g., clear or translucent, to allow actinic radiation to pass through it to the scaffold in order to crosslink the scaffold.

Although top plate 171 is illustrated as a flat plate, the topography of this compressive element can take any desirable shape and/or curvature to ensure that the arrangements of the collagen fibrils are properly fixed to build a lenticule of a desired shape, which can again be preserved or fixed by radiation-induced crosslinking.

Figure 13:
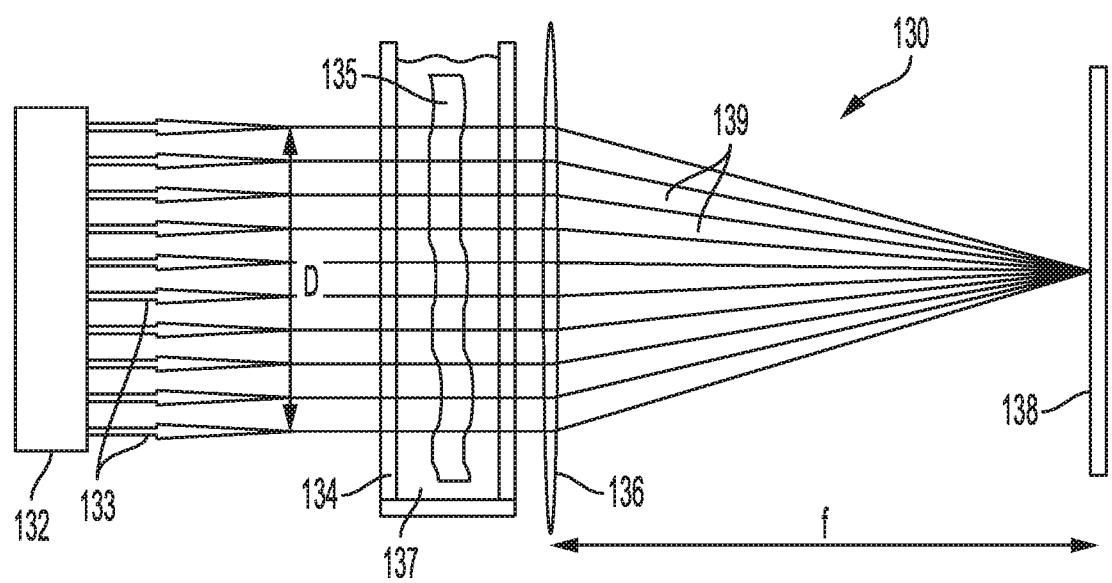
FIG. 13 illustrates an apparatus for measuring the transparency of lenticules produced in accordance with the disclosure.

FIG. 13 illustrates an apparatus 130 for measuring the transparency of lenticules produced in accordance with the disclosure. The apparatus 130 includes a light source 132, a cuvette 134 (into which a lenticule 135 can be placed), lens 136 and detector 138. The light source, e.g., a light-emitting diode (LED) with a waveguide/fiber and beam collimator (not shown), preferably produces a beam of collimated light rays 133. The beam should be spatially coherent with a flat (non-Gaussian) intensity profile across its beam width D (e.g., about 5-7 mm). For example, the light source 132 can produce green light with a center wavelength of about 500 nanometers and a bandwidth of about 5-10 nanometers.

The light from source 132 is directed to cuvette 134 in which lenticule 135 is suspended in a refractive index matching fluid 137 (e.g., a silicone oil or other fluid having an index of refraction, n, of about 1.376, that is immiscible with water and chemically inert). (The value of n=1.376 represents the nominal or average index of refraction for native corneal tissue.) In some instances, it can be advantageous to have a lenticule with a different index of refraction. In such cases, the fluid in the cuvette would be chosen to match the specific n value of the lenticule undergoing testing. The light that passes through the cuvette 134 (and lenticule 135) is then directed to lens 136 which is a high quality lens, free of spherical aberrations at the chosen beam wavelength. The lens 136 has a focal length, f, and serves to direct focused light onto detector 138 situated in the focal plane of the lens 136. If the transparency of the lenticule is perfect (and assuming ideal optical transparency for the optical elements through which light from the source 132 passes to the detector 138), the size of the beam impinging among the detector (situated at the focal plane) would be a diffraction-limit spot of uniform intensity. In actuality, the lenticule will not be perfectly transparent and beam intensity image at the detector will exhibit some amount of blurring due to forward scattering of light in the scaffold. (The focal length of the lens, together with the beam diameter, should be chosen to impose the desired diffraction-limited angular resolution.)

Transparency of the lenticule can thus be measured by measuring the intensity profile of the detected beam. Suitable photodetectors for measuring the intensity or brightness profiles can include, for example, photographic plates, CCD arrays or scanning pinhole detectors.

Figure 14:
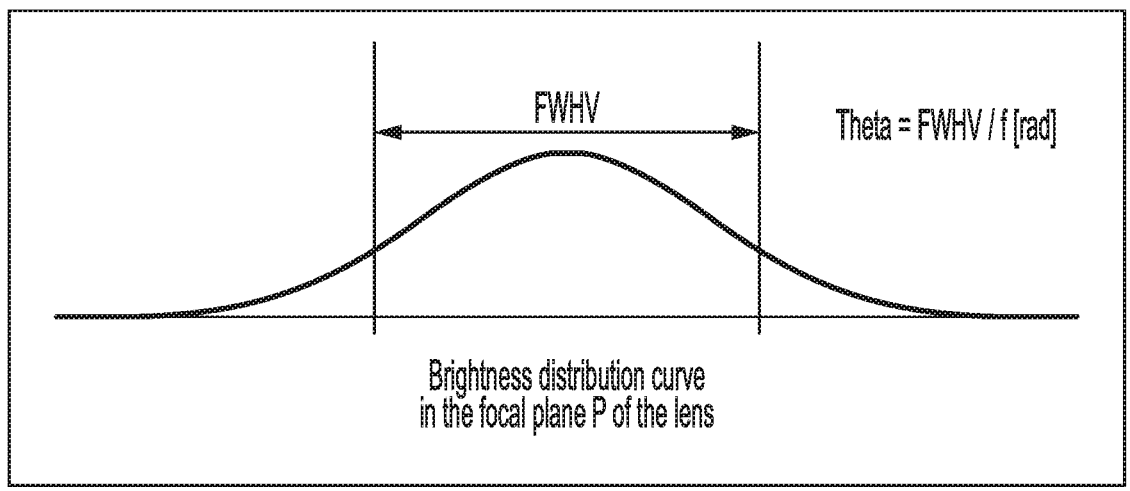
FIG. 14 is a graph of a brightness distribution curve obtainable with the apparatus of FIG. 13, or the like, in order to quantify optical clarity.

FIG. 14 is an illustration of such a method of quantifying transparency by measuring the lenticule's scattering angle (referred herein as "Θ" or "theta"). FIG. 14 illustrates a brightness distribution curve as measured in the focal plane of the lens. This Gaussian-like distribution represents the sum of all the contributions of scattered wave fronts. The more scattering in the lenticule, the larger the width of the detected beam. One measure of scattering (the degradation of optical clarity) is the full-width, half vertical maximum (FWHV) as shown in FIG. 14. (It should be understood that the Gaussian-like curve of FIG. 14 is an idealization and real brightness curves can be distorted by noise or other spurious signals.) Multiple measurements and averaging (or other known noise reducing signal processing techniques) can be used to obtain the best data representation of scattering by the lenticule. The FWHV value divided by the focal length, f, provides a measurement of the angular spread of the beam (in radians):

Θ=FWHV/f[rad]

Theta is dependent only on the amount of scattering and can also be expressed in terms of arcminutes using the conversion formula: 1 arcmin=291 microrad. Lenticules manufactured by the methods disclosed herein exhibit satisfactory transparency (e.g., for intracorneal implantation) if the angle Θ is less than 4 arcminutes, preferably, less than 3 or 2 arcminutes, more preferably in some instances, less than 1 arcminute.

As noted previously, crosslinking can also be used advantageously to modify the "stiffness" of the lenticules and scaffolds. Lenticules and scaffolds of increased stiffness can be obtained by the present teachings. The stiffness of the crosslinked collagen can be quantified, for example, by the parameter, μ, called modulus. The nominal standard value for the modulus, μ, of native human corneal collagen depending on age is about $4 \times 10^4$ Pascal (Pa) to about $1.2 \times 10^5$ Pa. Moreover, for porcine eyes (which can be an important source of implantable lenticular and scaffold collagen) the average modulus, μ, of corneal collagen can be as low as about $2 \times 10^4$ Pascal (Pa).

As a result of compaction and crosslinking according to the present teachings, collagenous lenticules and scaffolds can be obtained exhibit a modulus stiffness, μ, greater than $2 \times 10^4$ Pa, or greater than $8 \times 10^4$ Pa, or greater than $1.6 \times 10^5$ Pa, or greater than $2 \times 10^5$ Pa, or greater than $3 \times 10^5$ Pa, or greater than $5 \times 10^5$ Pa, or greater than $8 \times 10^5$ Pa, or greater than $1 \times 10^6$ Pa, or greater than $3 \times 10^6$ Pa, or greater than $5 \times 10^6$ Pa, or greater than $1 \times 10^7$ Pa.

For example, lenticules (including scaffolds) according to the present teachings can exhibit a modulus value, μ, ranging from $1 \times 10^4$ Pa to $1 \times 10^7$ Pa, or from $2 \times 10^4$ Pa to $8 \times 10^6$ Pa, or from $1 \times 10^5$ Pa to $5 \times 10^6$ Pa, or from $3 \times 10^5$ Pa to $5 \times 10^6$ Pa, or from $1 \times 10^6$ Pa to $2.6 \times 10^6$ Pa.

Various techniques for measuring the increased stiffness (higher modulus, μ) of crosslinked collagen will be apparent to one or ordinary skill in the art. For example, the instruments of FIGS. 15A-15B and 16A-16B are illustrative.

Figure 15A:
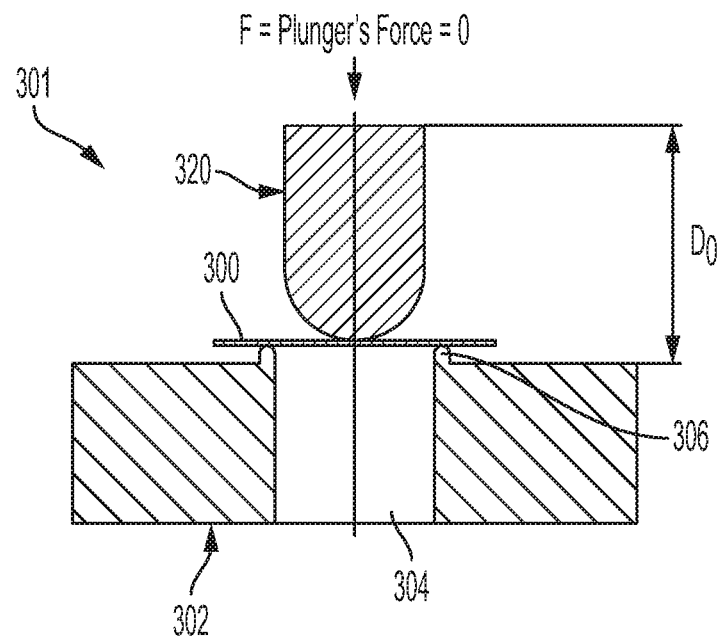
FIG. 15A is a schematic cross-sectional view of an instrument for measuring the stiffness (modulus, $\mu$) of a planar compressed/compacted and crosslinked lenticule in accordance with the disclosure in its initial non-stressed state.
Figure 15B:
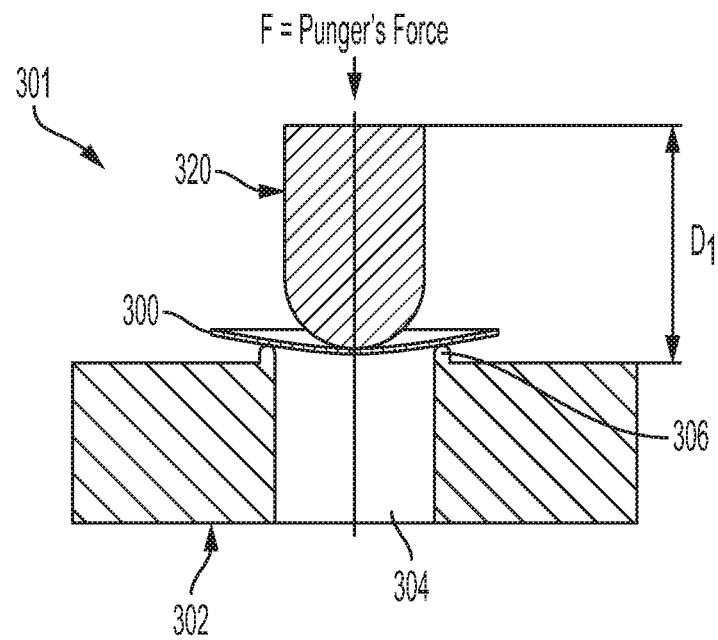
FIG. 15B is a schematic cross-sectional view of the instrument of FIG. 15A upon application of a test force.

In FIGS. 15A-15B, an instrument 301 for measuring the stiffness of a flat crosslinked lenticule 300 is shown comprising a pedestal 302 having an inner hole 304 with a circular rim 306. The lenticule 300 to be tested is placed on the pedestal and spanning the rim 306. Plunger 320 of a defined weight and geometry is set at an initial distance Do just in contact with the lenticule 300. Lenticule 300 will typically have a diameter from about 6 to about 9 millimeters and a thickness of about 0.1 millimeters (100 micrometers). The diameter circular rim (the hole size) 306 can be about 5 millimeters and the radius of curvature of the rim itself can be, for example, about 0.2 millimeters (200 micrometers). The diameter of the plunger 320 can be, for example, about 4 millimeters. In some aspects, for example when measuring the stiffness of a weakened lenticule, the diameter of the circular rim (the hole size) 306 can be about 2 millimeters, and the diameter of the plunger 320 can be about 1 millimeter, by way of non-limiting example.

When initially placed in contact with the lenticule, the force applied by the plunger is zero. Preferably, the pedestal rim and the plunger are formed from a materials with a low coefficient of friction, such as polytetrafluoroethylene (PTFE) or polyetheretherketone (PEEK). A defined force can be applied to the lenticule 300 by the plunger 320 to stretch the lenticule 300 downward and the distance traveled by the plunger ($D_1$) can be measured. From this distance D1, the modulus, μ, can be derived. Alternatively, the plunger 300 can be moved a defined distance $D_1$ and the counterforce experienced by the plunger measured to derive the modulus, μ.

Figure 16A:
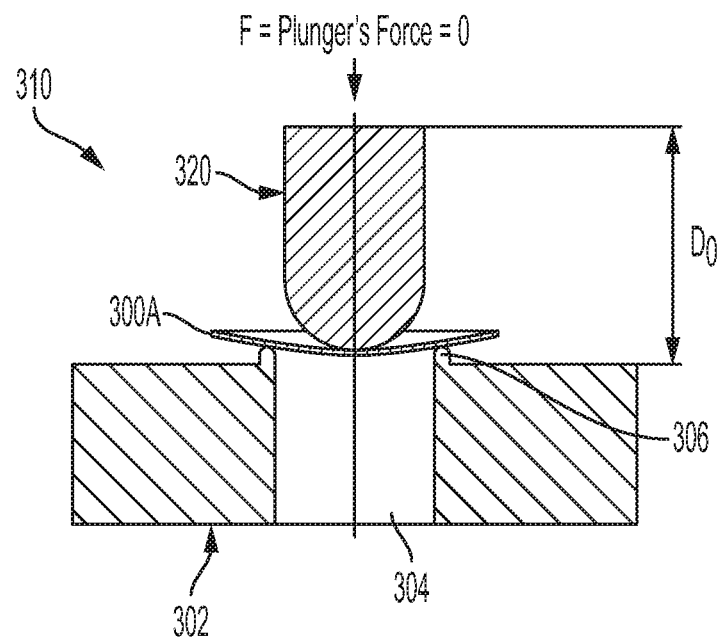
FIG. 16A is a schematic cross-sectional view of an instrument for measuring the stiffness (modulus, μ) of a non-planar, compressed/compacted and crosslinked lenticule in accordance with the disclosure in its initial non-stressed state.
Figure 16B:
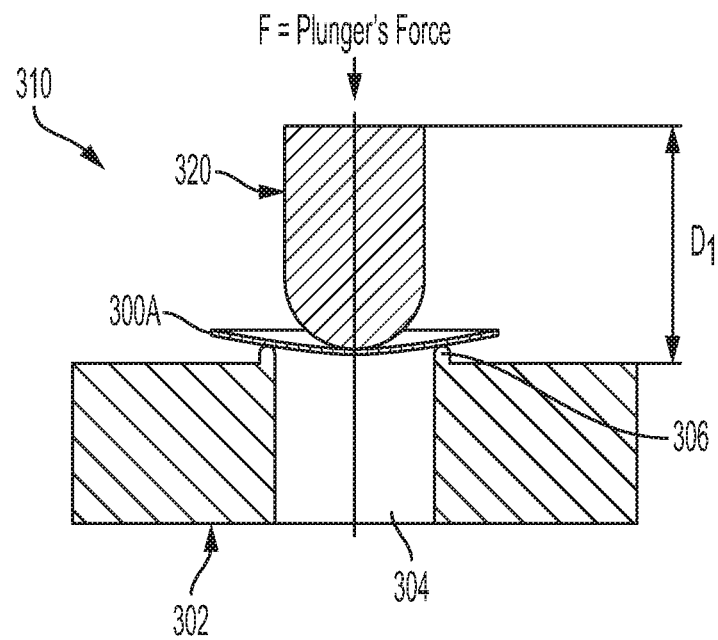
FIG. 16B is a schematic cross-sectional view of the instrument of FIG. 16A upon application of a test force.

In FIGS. 16A-16B, a similar instrument 310 is shown for measuring the stiffness of a crosslinked lenticule 300A having a nonplanar shape (e.g., a lenticule with either a curved anterior surface or a curved posterior surface (or both)). The instrument 310 again comprises a pedestal 302 having an inner hole 304 with a circular rim 306 of similar dimensions. The lenticule 300A to be tested is similarly placed above the pedestal and spanning the rim 306. Plunger 320 is again set at an initial distance $D_0$ just in contact with the lenticule 300A. The force initially applied by the plunger 320 is again zero. In a manner similar to that described above in connection with FIGS. 15A-15B, a defined force is applied to the plunger 320 or the plunger 300 is moved a defined distance $D_1$ to stretch the lenticule 300A downward. From distance traveled by the plunger ($D_1$) or a measurement of the counterforce experienced by the plunger, the modulus, μ, of lenticule 300A can likewise be derived.

All patent literature or publications cited herein are incorporated in their entirety by reference. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art. Any element or feature shown in connection with one embodiment can be used interchangeably with, in combination with, or in addition to, any element or feature shown in any other embodiment and all such permutations of elements and features should be understood to be encompassed by the disclosure. Accordingly, it will be understood that the invention is not to be limited to the embodiments disclosed herein, but is to be understood from the following claims, which are to be interpreted as broadly as allowed under the law.

The invention claimed is:

1. A method of forming a scaffold from donor corneal stroma excised from a central region of a donor corneal source comprising:
   decellularizing donor corneal stroma to obtain a scaffold;
   exerting a mechanical pressure on the scaffold to compress the scaffold so as to remove at least a portion of fluid present in the scaffold and to densify at least a portion of collagen fibril bundles thereof so as to form a compacted scaffold having a thickness in a range of about 600 micrometers to about 15 micrometers and exhibiting a collagen concentration of at least 20% for intrastromal implantation, wherein the collagen concentration is measured as a fractional weight of the scaffold in a desiccated state relative to a weight of the scaffold in a state in full equilibrium with water; and
   crosslinking at least a portion of the collagen fibril bundles of the scaffold while the scaffold is maintained in a compacted state to enhance axial mechanical strength of the scaffold,
   wherein said removing fluid and crosslinking are performed such that the compacted, crosslinked scaffold substantially retains layered collagen arrangement of the donor corneal stroma and as a result, the scaffold exhibits sufficient optical clarity for use in intrastromal implantation.

2. The method of claim 1 wherein the step of exerting a mechanical pressure to remove at least a portion of the fluid includes cycles of repeated removal of at least a portion of the fluid followed by rehydration.

3. The method of claim 1 wherein the step of decellularizing further comprises treating the scaffold with a chemical decellularizing agent and the step of decellularizing occurs before removing the fluid, and the step of crosslinking occurs when the compacted scaffold is under said mechanical pressure.

4. The method of claim 1 wherein the step of decellularizing further comprises removing cellular debris from the scaffold with a detergent or a surfactant.

5. The method of claim 4 wherein the method further comprises enzymatically removing or conformationally altering at least one immunogenic epitope of the scaffold.

6. The method of claim 1 wherein the crosslinked scaffold exhibits a collagen concentration of at least 40 percent.

7. The method of claim 1 wherein the step of crosslinking further comprises exposing at least a portion of the compressed scaffold to a crosslinking promoter or actinic radiation.

8. The method of claim 1 wherein the step of crosslinking further comprises exposing at least a portion of the compressed scaffold to radiation to induce crosslinking by peptide bond formation between collagen fibrils with or without the assistance of a crosslinking promoter or other energy mediating agent and optionally wherein the step of crosslinking the scaffold further comprises irradiating the scaffold with ultraviolet radiation, x-rays, gamma radiation or an electron beam.

9. The method of claim 8 wherein the step of crosslinking further comprises exposing at least a portion of the compressed scaffold to ultraviolet radiation by direct exposure, or by exposure at a grazing incidence angle or via an evanescent waveguide coupled to a surface of the scaffold.

10. The method of claim 8 wherein the step of crosslinking further comprises selectively exposing a surface portion of the compressed scaffold to a radiation such that the surface portion exhibits greater crosslinking and higher collagen density than a bulk region of the scaffold.

11. The method of claim 8 wherein the step of crosslinking further comprises applying sufficient radiation to inactivate any microbial agents and/or sterilize the scaffold.

12. The method of claim 1, wherein the scaffold is configured for use as an implantable lenticule having a lenticule body, an anterior surface and a posterior surface that give the lenticule a final desired shape.

13. The method of claim 12, wherein the step of crosslinking further comprises treating at least a portion of the posterior surface of the lenticule with a crosslinking agent or by selective application of patterning radiation to promote adherence of the lenticule to a stromal bed when implanted into a patient's stromal bed.

14. The method of claim 1, wherein the step of crosslinking further comprises enhancing the optical clarity of the scaffold.

15. The method of claim 14 wherein the scaffold exhibits a scattering angle, theta, of less than 4 arcminutes.

16. The method of claim 15 wherein the scaffold exhibits a scattering angle, theta, of less than 3 arcminutes or less than 2 arcminutes, or less than 1 arcminute.

17. The method of claim 1 wherein the scaffold exhibits a modulus stiffness, $\mu$, greater than $1.2 \times 10^5$ Pa.

18. The method of claim 1 wherein the scaffold exhibits a modulus stiffness, u, greater than $1.4 \times 10^5$ Pa, or greater than $1.6 \times 10^5$ Pa, or greater than $1.8 \times 10^5$ Pa, or greater than $2 \times 10^5$ Pa, or greater than $3 \times 10^5$ Pa, or greater than $5 \times 10^5$ Pa, or greater than $8 \times 10^5$ Pa, or greater than $1 \times 10^6$ Pa, or greater than $2 \times 10^5$ Pa or greater than $2.6 \times 10^6$ Pa, or greater than $3 \times 10^6$ Pa, or greater than $4 \times 10^6$ Pa.

19. A method of forming a crosslinked collagenous scaffold derived from a donor corneal stroma with reduced application of radiation, the method comprising:
obtaining a collagenous scaffold from donor corneal stroma;
removing at least a portion of fluid present in the scaffold by exerting a mechanical pressure on the scaffold to compress the scaffold s and form a compacted scaffold exhibiting a collagen concentration of at least 20% for intrastromal implantation, wherein the collagen concentration is measured as a fractional weight of the scaffold in a desiccated state relative to a weight of the scaffold in a state in full equilibrium with water; and
crosslinking at least a portion of the scaffold by subjecting the scaffold to radiation while the scaffold is maintained in a compacted state to define a final desired shape and enhance axial mechanical strength of the scaffold,
wherein said removing fluid and crosslinking steps are performed such that the compacted, crosslinked scaffold substantially retains layered collagen arrangement of the donor corneal stroma and as a result, the scaffold exhibits sufficient optical clarity for use as an intrastromal implant,
wherein the step of crosslinking of the at least a portion of the scaffold is performed without assistance of an energy mediating agent.

20. A method of forming a scaffold from donor corneal stroma excised from a central region of a donor corneal source comprising:
decellularizing donor corneal stroma to obtain a scaffold;
removing at least a portion of fluid present in the scaffold by applying a mechanical pressure on the scaffold to compact collagen fibrils of the scaffold into densified collagen fibril bundles and obtain a concentration of at least 20% for the collagen fibrils within the scaffold, wherein the concentration of the collagen fibrils is measured as a fractional weight of the scaffold in a desiccated state relative to a weight of the scaffold in a state in full equilibrium with water,
crosslinking at least a portion of the densified collagen fibril bundles via application of UV radiation to said collagen fibril bundles at a fluence of less than 2500 Joules/cm$^2$ to enhance axial mechanical strength of the scaffold, wherein the compacting and crosslinking are performed such that the compacted, crosslinked scaffold substantially retains layered collagen arrangement of the donor corneal stroma and as a result, the scaffold exhibits sufficient optical clarity for use in intrastromal implantation.

21. The method of claim 1, wherein the step of exerting a mechanical pressure to remove at least a portion of fluid present in the scaffold comprises using a movable compression exerting element to compress the scaffold.

22. The method of claim 21, wherein said movable compression exerting element comprises a first press element of a press in which the scaffold is positioned.

23. The method of claim 22, wherein the press comprises a movable stage configured to hold the first press element, and wherein the press further comprises a second press element such that the first and the second press elements are configured to cooperatively apply a compressive force to the scaffold.

24. The method of claim 23, wherein at least one of said first and said second press elements is non-planar and shaped to conform to a desired final shape of the scaffold.

25. The method of claim 23, further comprising positioning the scaffold in the press and applying a motive force to the movable stage to cause compression of the scaffold via said first press element so as to perform the step of removing at least a portion of fluid present in the scaffold.

26. The method of claim 25, wherein at least one of the first and the second press elements is transparent or translucent to an actinic radiation, and further comprising applying the actinic radiation through said transparent or translucent press element to said scaffold to perform the step of cross-linking at least a portion of the scaffold.

27. The method of claim 26, wherein said actinic radiation has a wavelength in a range of about 193 nm to about 400 nm.

28. The method of claim 21, wherein the step of exerting a mechanical pressure to remove at least a portion of the fluid present in the scaffold comprises placing the scaffold in a mold configured to compress the scaffold.

29. The method of claim 28, wherein the mold comprises a top portion and bottom portion between which the scaffold is placed.

30. The method of claim 29, wherein at least one of the top portion and the bottom portion of the mold is transparent or translucent to an actinic radiation, and further comprising applying the actinic radiation through said at least one of the top and the bottom transparent or translucent portion to said scaffold to perform the step of cross-linking at least a portion of the scaffold.

31. The method of claim 30, wherein said actinic radiation has a wavelength in a range of about 193 nm to 400 nm.

32. The method of claim 1, wherein the compacted scaffold exhibits a collagen concentration of at least 25% or at least 30% or at least 35%.

33. The method of claim 1, wherein the compacted scaffold exhibits a collagen concentration between 20% and 75%.

34. The method of claim 19, wherein the compacted scaffold exhibits a collagen concentration of at least 30% or at least 35%.

35. The method of claim 19, wherein the compacted scaffold exhibits a collagen concentration between 20% and 75%.

36. The method of claim 20, wherein the compacted scaffold exhibits a collagen concentration of at least 30% or at least 35%.

37. The method of claim 20, wherein the compacted scaffold exhibits a collagen concentration between 20% and 75%.

* * * * *